US008299211B2

(12) United States Patent
Best et al.

(10) Patent No.: US 8,299,211 B2
(45) Date of Patent: *Oct. 30, 2012

(54) PEPTIDES AND REGULATION OF CALCIUM CHANNELS

(75) Inventors: Philip M. Best, Urbana, IL (US); Ren-Shiang Chen, Miami, FL (US); Zuojun Lin, King of Prussia, PA (US); Thomas Garcia, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 539 days.

This patent is subject to a terminal disclaimer.

(21) Appl. No.: 12/429,214

(22) Filed: Apr. 24, 2009

(65) Prior Publication Data

US 2009/0325887 A1 Dec. 31, 2009

Related U.S. Application Data

(63) Continuation-in-part of application No. 11/537,323, filed on Sep. 29, 2006, now Pat. No. 8,022,177.

(60) Provisional application No. 61/047,929, filed on Apr. 25, 2008, provisional application No. 60/722,707, filed on Sep. 30, 2005.

(51) Int. Cl.
*A61K 38/00* (2006.01)
*C07H 21/04* (2006.01)
*C12P 21/06* (2006.01)
*C12N 5/00* (2006.01)

(52) U.S. Cl. ...... 530/324; 514/12.1; 536/23.5; 435/69.1

(58) Field of Classification Search .................. None
See application file for complete search history.

(56) References Cited

U.S. PATENT DOCUMENTS

| | | | |
|---|---|---|---|
| 4,925,664 A | 5/1990 | Jackson et al. |
| 5,122,596 A | 6/1992 | Phillips et al. |
| 5,281,693 A | 1/1994 | Jackson et al. |
| 5,364,842 A | 11/1994 | Justice et al. |
| 5,512,592 A | 4/1996 | Zaloga et al. |
| 5,585,396 A | 12/1996 | Zaloga et al. |
| 5,599,559 A | 2/1997 | Phillips et al. |
| 5,677,288 A | 10/1997 | Marangos |
| 5,756,663 A | 5/1998 | Lampe |
| 5,776,896 A | 7/1998 | Lampe |
| 5,795,864 A | 8/1998 | Amstutz et al. |
| 5,807,821 A | 9/1998 | Lampe |
| 5,877,026 A | 3/1999 | Lampe |
| 5,968,838 A | 10/1999 | Lampe et al. |
| 6,011,035 A | 1/2000 | Snutch et al. |
| 6,063,819 A | 5/2000 | Marangos et al. |
| 6,267,945 B1 | 7/2001 | Zamponi |
| 6,310,059 B1 | 10/2001 | Snutch |
| 6,365,337 B1 | 4/2002 | Letts et al. |
| 6,387,897 B1 | 5/2002 | Snutch |
| 6,492,375 B2 | 12/2002 | Snutch |
| 6,617,322 B2 | 9/2003 | Snutch |
| 6,943,168 B2 | 9/2005 | Snutch et al. |
| 6,949,554 B2 | 9/2005 | Snutch et al. |
| 8,022,177 B2 | 9/2011 | Best et al. |
| 2004/0034035 A1 | 2/2004 | Snutch et al. |
| 2004/0044004 A1 | 3/2004 | Snutch et al. |
| 2005/0014748 A1 | 1/2005 | Pajouhesh et al. |
| 2005/0203040 A1 | 9/2005 | Richards et al. |
| 2005/0209179 A1 | 9/2005 | McSwiggen et al. |
| 2005/0209180 A1 | 9/2005 | Jadhar et al. |
| 2007/0213267 A1 | 9/2007 | Best et al. |

FOREIGN PATENT DOCUMENTS

WO    WO 2007/041360    4/2007

OTHER PUBLICATIONS

Ahern et al. (2001) "Modulation of L-Type Ca2+ Current but Not Activation of Ca2+ Release by the Gamma-1 Subunit of the Dihydropyridine Receptor of Skeletal Muscle," *BMC Physiol.* 1(1):8.
Arikkath et al. (2003) "Auxiliary Subunits: Essential Components of the Voltage-Gated Calcium Channel Complex," *Curr. Opin. Neurobiol.* 13:298-307.
Arikkath et al. (2003) "Gamma 1 Subunit Interactions within the Skeletal Muscle L-Type Voltage-Gated Calcium Channels," *J. Biol. Chem.* 278:1212-9.
Arselin et al. (2003) "The GXXXG Motif of the Transmembrane Domain of Subunit e is Involved in the Dimerization/Oligomaerization of the Yeast ATP Synthase Complex in the Mitochondrial Membrane," *Eur. J. Biochem.* 270:1875-1884.
Bahinski et al. (1997) "Charged Amino Acids Near the Pore Entrance Influence Ion-Conduction of a Human L-Type Cardiac Calcium Channel," *Mol. Cell. Biochem.* 166(1-2):125-134.
Bartels et al. (2008) "Pos Different Structure-Function Relationship Determine Biophysical Properties and Pharmacological Modulation of T-Type Calcium Channels Cav3.1 and Cav3.2," *Biophys. J Meeting Abstracts* No. 3111, p. 1041, Feb. 2008.
Best et al. (Jan. 2006) "Identification of Critical Residues in TM1 of the Gamma-6 Subunit Critical for its Inhibitory Effect on Cav3.1 Calcium Current," *Biophysical Society* Poster 1906-Pos.
Black JL, 3rd (2003) "The Voltage-Gated Calcium Channel Gamma Subunits: a Review of the Literature," *J. Bioenerg. Biomembr.* 35(6):649-60.
Black et al. (1999) "Identification and Cloning of Putative Human Neuronal Voltage-Gated Calcium Channel Gamma-2 and Gamma-3 Subunits: Neurologic Implications," *Mayo Clin. Proc.* 74(4):357-361.
Burgess et al. (1999) "Identification of Three Novel Ca(2+) Channel Gamma Subunit Genes Reveals Molecular Diversification by Tandem and Chromosome Duplication," *Genome Res.* 9(12):1204-1213.
Burgess et al. (2001) "A Cluster of Three Novel Ca(2+) Channel gamma Subunit Genes on Chromosome 19q13.4: Evolution and Expression Profile of the gamma Subunit Gene Family," *Genomics* 71:339-350.

(Continued)

*Primary Examiner* — Kagnew H Gebreyesus
(74) *Attorney, Agent, or Firm* — Greenlee Sullivan P.C.

(57) ABSTRACT

Calcium channels can be regulated by natural gamma proteins. Herein we disclose embodiments of compositions and methods, particularly involving short peptides which are capable of regulating calcium channel function. Certain short peptides which can inhibit calcium current have structural features from the first transmembrane domain of gamma6 such as a GxxxA motif and adjoining aliphatic residues. In embodiments the peptide compositions and methods are capable of selective efficacy for low voltage-activated calcium channels, such as LVA channel Cav3.1, versus high voltage-activated channels.

28 Claims, 8 Drawing Sheets

OTHER PUBLICATIONS

Cabral et al. (Apr. 3, 2009) "Glutamate Receptor Antagonism in Inferior Colliculus Attenuates Elevated Startle Response of High Anxiety Diazepam-Withdrawn Rats," *Neuroscience* 161:707-717.

Campbell et al. (1988) "Structural Characterization of the Nitrendiphine Receptor of the Voltage-Dependent Ca2+ Channel: Evidence for a 52,000 Da Subunit," *J. Cardiovasc. Pharmacol.* 12(4):S86-S90.

Catterall, W.A. (2000) "Structure and Regulation of Voltage-Gated Ca2+ Channels," *Ann. Rev. Cell. Dev. Biol.* 16:521-555.

Catterall, W.A. (1988) "Molecular Properties of Voltage-Sensitive Sodium and Calcium Channels," *Braz. J. Med. Biol. Res.* 21(6):1129-1144.

Chen et al. (2000) "Stargazin Regulates Synaptic Targeting of AMPA Receptors by Two Distinct Mechanisms," *Nature* 408:936-943.

Chen et al. (2007) "Calcium Channel Gamma Subunits: A Functionally Diverse Protein Family," *Cell. Biochem. Biophys.* 47:178-186.

Chen et al. (Feb. 4, 2009) A Small Peptide Inhibitor of the Low Voltage-Activated Calcium Channel Cav3.1. Published on Feb. 4, 2009 as doi:10.1124/mol.108.052654, MOL #52654, Running title: A Peptide Inhibitor of the Cav3.1 Channel.

Chen et al. (May 2009) "A Small Peptide Inhibitor of the Low Voltage-Activated Calcium Channel Cav3.1," *Mol. Pharmacol.* 75(5):1042-1051.

Chiang et al. (2009) "The $Ca_v3.2$ T-Type $Ca^{2+}$ Channel is Required for Pressure Overload-Induced Cardiac Hypertrophy in Mice," *Circ. Res.* 104:522-530.

Chinault et al. (Apr. 16, 2004) "Subunits of a Yeast Oligomeric G Protein-Coupled Receptor are Activated Independently by Agonist but Function in Concert to Activate G Protein Heterotrimers," *J. Biol. Chem.* 279(16):16091-16100.

Chu et al. (2001) Calcium Channel Gamma Subunits Provide Insights into the Evolution of this Gene Family. *Gene* 280:37-48.

Claycomb et al. (1998) "HL-1 Cells: A Cardiac Muscle Cell Line that Contracts and Retains Phenotypic Characteristics of the Adult Cardiomyocyte," *Proc. Nat. Acad. Sci. USA* 95(6):2979-2984.

Costagliola et al. (2002) "Tyrosine Sulfonation is Required for Agonist Recognition by Glycoprotein Hormone Receptors," *EMBO J.* 21(4):504-513.

Curran et al. (2003) "Sequence Motifs, Polar Interactions and Conformational Changes in Helical Membrane Proteins," *Curr. Opin. Struct. Biol.* 13:412-417.

Curtis et al. (1984) "Purification of the Calcium Antagonist Receptor of the Voltage-Sensitive Calcium Channel from Skeletal Muscle Transverse Tubules," *Biochem.* 23(10):2113-2118.

De Jongh et al. (1991) "Characterization of the Two Size Forms of the Alpha 1 Subunit of Skeletal Muscle L-Type Calcium Channels," *Proc. Nat. Acad. Sci USA* 88(23):10778-10782.

De Waard et al. (1996) "Structural and Functional Diversity of Voltage-Activated Calcium Channels," *Ion Channels* 4:41-87.

De Waard et al. (1994) "Ca2+ Channel Regulation by a Conserved Beta Subunit Domain," *Neuron.* 13(2):495-503.

De Waard et al. (1996) "Identification of Critical Amino Acids Involved in Alpha 1-Beta Interaction in Voltage-Dependent Ca2+ Channels," *FEBS Lett.* 380(3):272-276.

Dolphin AC (2003) "Beta Subunits of Voltage-Gated Calcium Channels," *J. Bioenerg. Biomembr.* 35:599-620.

Doura et al. (2004) "Sequence Context Modulates the Stability of GxxxG-Mediated Transmembrane Helix-Helix Dimer," *J. Mol. Biol.* 341(4):991-998.

Dubel et al. (2004) "Plasma Membrane Expression of T-Type Calcium Channel Alpha 1 Subunits is Modulated by HVA Auxiliary Subunits," *J. Biol. Chem.* 279:29263-29269.

Eberst et al. (1997) "Identification and Functional Characterization of a Calcium Channel Gama Subunit," *Pflugers Arch.* 433(5):633-637.

El Amri et al. (Mar. 2008) "Plasticins: Membrane-Damaging Peptides with 'Chameleon-Like' Properties," *Cell Mol. Life Sci.* 65(6):895-909.

Ertel et al. (2000) "Nomenclature of Voltage-Gated Calcium Channels," *Neuron* 25:533-535.

Fletcher et al. (1998) "Genetic Analysis of Voltage Dependent Calcium Channels," *J. Bioeng. Biomembr.* 30(4):387-398.

Flockerzi et al. (1986) "Purified Dihydropyridine-Binding Site from Skeletal Muscle T-Tubules is a Functional Calcium Channel," *Nature* 323:66-68.

Freise et al. (2000) "Absence of the Gamma Subunit of the Skeletal Muscle Dihydropyridine Receptor Increases L-type Ca2+ Currents and Alters Channel Inactivation Properties," *J. Biol. Chem.* 275:14476-14481.

Friel et al. (Jan. 1988) Two ATP-Activated Conductances in Bullfrog Atrial Cells (citing Yellen G. Nature. Mar. 25, 1982;296(5855):357-9, Single Ca2+-Activated Nonselective Cation Channels in Neuroblastoma (discusses 'sewer-pipe' technique)) *J. Gen Physiol.* 91:1-27.

Gerber et al. (May 14, 2004) "Two Motifs within a Transmembrane Domain, One for Homodimerization and the Other for Heterodimerization," *J. Biol. Chem.* 279(20):21177-21182.

Gorman et al. (2008) "Dimerization of the Transmembrane Domain of Amyloid Precursor Proteins and Familial Alzheimer's Disease Mutants," *BMC Neurosci.* 9:17.

Green, P. (2001) "Kinetic Modification of the Alpha1I Subunit-Mediated T-Type Ca2+ Channel by a Human Neuronal Ca2+ Channel Gamma Subunit," *J. Physiol.* 533(2):467-478.

Gurnett et al. (1997) "Extracellular Interaction of the Voltage Dependant Ca2+ Channel Alpha 2 Delta and Alpha 1 Subunits," *J. Biol. Chem.* 272(29):18508-18512.

Hansen et al. (2004) "Calcium Channel Gamma6 Subunits are Unique Modulators of Low Voltage-Activated (Cav3.1) Calcium Current," *J. Mol. Cell. Cardiol.* 37:1147-1158.

Held et al. (2002) "Skeletal Muscle L-Type Ca(2+) Current Modulation in Gamma1-Deficient and Wildtype Murine Myotubes by the Gamma1 Subunit and cAMP," *J. Physiol.* 539:459-468.

Hofmann et al. (1999) "Voltage-Dependent Calcium Channels: From Structure to Function," *Rev. Phys. Biochem. Pharmacol.* 139(2):33-87.

Huang et al. (2000) "Reexpression of T-type Ca2+ Channel Gene and Current in Post-Infarction Remodeled Rat Left Ventricle," *Cardiovasc. Res.* 46:442-449.

Humphrey et al. (1996) "VMD—Visual Molecular Dynamics," *J. Mol. Graphics* 14:33-38.

International Search Report, Corresponding to International Application No. PCT/US06/38179, Mailed Apr. 16, 2008.

Jangsangthong et al. (2008) "Pos Competition Between Beta-Subunits of Cardiac L-Type Calcium Channels at Single Channel Level," *Biophys. J. Meeting Abstract*, Poster No. 3127, p. 1047, Feb. 2008.

Jay et al. (1990) "Primary Structure of the Gamma Subunit of the DHP-Sensitive Calcium Channel from Skeletal Muscle," *Science* 248:490-492.

Kairys et al. (Jun. 2004) "Structural Model for an AxxxG-Mediated Dimer of Surfactant-Associated Protein C," *Eur. J. Biochem.* 271(11):2086-2092.

Kang et al. (2001) "Biochemical and Biophysical Evidence for Gamma 2 Subunit Association with Neuronal Voltage-Activated $Ca^{2+}$ Channels," *J. Biol. Chem.* 276(35):32917-32924.

Kang et al. (2003) "Gamma Subunit of Voltage-Activated Calcium Channels," *J. Biol. Chem.* 2778(24):21315-21318.

Kato et al. (Sep. 2008) "AMPA Receptor Subunit-Specific Regulation by a Distinct Family of type II TARPs," 59(6):986-96.

Kleiger et al. (2002) "GXXXG and GXXXA Motifs Stabilize FAD and NAD(P)-Binding Rossmann Folds Through C(alpha)-H . . . O Hydrogen Bonds and van der Waals Interactions," *J. Mol. Biol.* 323:69-76.

Kleiger et al. (2002) "GXXXG and AXXXA: Common Alpha-Helical Interaction Motifs in Proteins, Particularly in Extremophiles," *Biochemistry* 41(19):5990-5997.

Klugbauer et al. (2003) "Calcium Channel Alpha2delta Subunits: Differential Expression, Function, and Drug Binding," *J. Bioenerg. Biomembr.* 35:639-647.

Klugbauer et al. (2000) "A Family of Gamma-Like Calcium Channel Subunits," *FEBS* 470(2):189-197.

Klugbauer et al. (1999) "Molecular Diversity of the Calcium Channel Alpha 2 Delta Subunit," *J. Neurosci.* 19(2):684-691.

Kobus et al. (Feb. 8, 2005) "The GxxxG-Containing Transmembrane Domain of the CCK4 Oncogene Does Not Encode Preferential Self-Interactions," *Biochemistry* 44(5):1464-1470.

Kuo et al. (1994) Slow binding of phenytoin to inactivated sodium channels in rat hippocampal neurons, Mol. Pharmacol 46(4):716-725.

Lacinova et al. (2004) "Modulation of Gating Currents of the Ca(v)3.1 Calcium Channel by Alpha 2 Delta 2 and Gamma 5 Subunits," *Arch. Biochem. Biohys.* 425(2):207-213.

Larsen et al. (2002) "Quantitative Analysis of the Expression and Distribution of Calcium Channel Alpha 1 Subunit mRNA in the Atria and Ventricles of the Rat Heart," *J. Mol. Cell. Cardiol.* 34:519-532.

Lear et al. (2004) "Association of a Model Transmembrane Peptide Containing gly in a Heptad Sequence Motif," *Biophys. J.* 87:3421-3429.

Lee et al. (2004) "A Membrane-Access Mechanism of Ion Channel Inhibition by Voltage Sensor Toxins from Spider Venom," *Nature* 430:232-235.

Lemmon et al. (Apr. 15, 1992) "Glycophorin A Dimerization is Driven by Specific Interactions Between Transmembrane α-Helices," *J. Biol. Chem.* 267(11):7683-7689.

Leonov et al. (2005) "A Periodicity Analysis of Transmembrane Helices," *Bioinformatics* 21(11):2604-2610.

Letts et al. (1998) "The Mouse Stargazer Gene Encodes a Neuronal $Ca^{2+}$-Channel Gamma Subunit," *Nat. Genet.* 19(4):340-347.

Leung et al. (1987) "Growth Hormone Receptor and Serum Binding Protein: Purification, Cloning and Expression," *Nature* 330:537-543.

Li et al. (2004) "Single-Channel Analysis of KCNQ $K^+$ Channels Reveals the Mechanism of Augmentation by Cysteine-Modifying Reagent," *J. Neurosci* 24(22):5079-5090.

Lin et al. (Nov. 15, 2008) "A Critical GxxxA Motif in the {gamma}6 Calcium Channel Subunit Mediates its Inhibitory Effect on Cav3.1 Calcium Current," *J. Physiol.* 586(22):5349-5366.

Lin, Zuojun (2005), The calcium channel γ6 (gamma 6) subunit—analysis of function and determination of a sequence motif critical for its effect, Doctoral dissertation, University of Illinois at Urbana-Champaign, Urbana, Illinois (according to the Graduate College, deposited on Dec. 2, 2005).

Liu et al. (2002) "Genomic Analysis of Membrane Protein Families: Abundance and Conserved Motifs," *Genome. Biol.* 3(10):Research0054.1-0054.12.

Martin et al. (2000) "Mibefradil block of cloned T-type calcium channels," J Pharm. Experimental Therapeutics 295(1):302-308.

McClain et al. (Apr. 4, 2003) "Essential Role of a GXXXG Motif for Membrane Channel Formation by *Helicobacter pylori* Vacuolating Toxin," *J. Biol. Chem.* 278 (14):12101-12108.

McCleskey EW (1994) "Calcium Channels: Cellular Roles and Molecular Mechanisms," *Curr. Opin. Neurobiol.* 4:304-312.

Melnyk et al. (2004) "The Affinity of GXXXG Motifs in Transmembrane Helix-Helix Interactions is Modulated by Long-Range Communication," *J. Biol. Chem.* 279(16):16591-16597.

Mendrola et al. (Feb. 15, 2002) "The Single Transmembrane Domains of ErbB Receptors Self-Associated in Cell Membranes," *J. Biol. Chem.* 277(7):4704-4712.

Milescu et al. (2007) "Tarantula Toxins Interact with Voltage Sensors within Lipid Membranes," *J. Gen. Physiol.* 130:497-511.

Moreno et al. (1997) "Beta Subunits Influence the Biophysical and Pharmacological Differences Between P- and Q-Type Calcium Currents Expressed in a Mammalian Cell Line," *Proc. Nat. Acad. Sci. USA* 94(25):14042-14047.

Moss et al. (2002) "The Novel Product of a Five-Exon Stargazin-Related Gene Abolishes Ca(V)2.2 Calcium Channel Expression," *Embo J.* 21:1514-1523.

Mottamal et al. (Feb. 8, 2005) "The Contribution of $C_\alpha$-H•••O Hydrogen Bonds to Membrane Protein Stability Depends on the Position of the Amide," *Biochemistry* 44(5):1607-1613.

Munter et al. (Mar. 21, 2007) "GxxxG Motifs within the Amyloid Precursor Protein Transmembrane Sequence are Critical for the Etiology of Abeta42," *EMBO J.* 26(6):1702-1712.

Neely et al. (1993) "Potentiation by the Beta Subunit of the Ratio of the Ionic Current to the Charge Movement in the Cardiac Calcium Channel," *Science* 262:575-578.

Njue et al. (2004) "Mutations in the Extracellular Domains of Glutamate-Gated Chloride Channel Alpha3 and Beta Subunits From Ivermectin-Resistant Cooperia Oncophora Affect Agonist Sensitivity," *J. Neurochem.* 89(5):1137-1147.

Nuss et al. (1993) "T-Type Ca2+ Current is Expressed in Hypertrophied Adult Feline Left Ventricular Myocytes," *Circ. Res.* 73(4):777-782.

Osten et al. (Jun. 2006) "Learning from Stargazin: The Mouse the Phenotype and the Unexpected," *Curr. Opin. Neurobiol.* 16(3):275-280.

Parthasarathy et al. (2008) "Transmembrane Helices that Form Two Opposite Homodimeric Interactions: An Asparagine Scan Study of αM and β2 Integrins," *Prot. Sci.* 17:930-938.

Pichler et al. (1997) "Beta Subunit Heterogeneity in Neuronal L-Type Ca2+ Channels," *J. Biol. Chem.* 272(21):13877-13882.

Pollack, A. (2005) "The Search for the Killer Painkiller," The New York Times Online Article, Feb. 15, 2005, http://www.nytimes.com2005/02/15/health/15pain,html?pagewanted=print&position=.

Pragnell et al. (1994) "Calcium Channel Beta-Subunit Binds to a Conserved Motif in the I-II Cytoplasmic Linker of the Alpha 1-Subunit," *Nature* 368:67-70.

Priel et al. (2005) "Stargazin Reduced Desensitization and Slows Deactivation of the AMPA-Type Glutamate Receptors," *J. Neurosci.* 25(10):2682-2686.

Qiao et al. (2003) "Nonchannel Functions of the Calcium Channel γ Subunit: Insight from Research on the Stargazer Mutant," *J. Bioeng. Biomembr.* 35(6):661-670.

Raybaud et al. (Dec. 22, 2006) "The Role of the $GX_9GX_3G$ Motif in the Gating of High Voltage-Activated Ca2+ Channels," *J. Biol. Chem.* 281(51):39424-39436.

Raybaud et al. (Dec. 21, 2007) "The Role of Distal S6 Hydrophobic Residues in the Voltage-Dependent Gating of CaV2.3 Channels," *J. Biol. Chem.* 282(38):27944-27952.

Roth et al. (2008) "Transmembrane Domain Interactions Control Biological Functions of Neuropilin-1," *Mol. Biol. Cell.* 19(2):646-654.

Rousset et al. (2001) "Functional Roles of Gamma-2, Gamma-3 and Gamma-4, Three New Ca2+ Channel Subunits, in P/Q-Type Ca2+ Channel Expressed in Xenopus Oocytes," *J. Physiol.* 532(3):583-593.

Russ et al. (2000) "The GxxxG Motif: A Framework for Transmembrane Helix-Helix Association," *J. Mol. Biol.* 296:911-919.

Schneider, D. (2004). "Rendezvous in a membrane: close packing, hydrogen bonding, and the formation of transmembrane helix oligomers." *FEBS Lett* 577(1-2):5-8.

Schneider et al. (2004) "Motifs of Two Small Residues can Assist but are not Sufficient to Mediate Transmembrane Helix Interactions," *J. Mol. Biol.* 343:799-804.

Scott et al. (1996) "Beta Subunit Heterogeneity in N-Type Ca2+ Channels," *J. Biol. Chem.* 271(6):3207-3212.

Senes et al. (2004) "Folding of Helical Membrane Proteins: The Role of Polar, GxxxG-Like and Proline Motifs," *Curr. Opin. Struct. Biol.* 14:465-479.

Senes et al. (2000) "Statistical Analysis of Amino Acid Patterns in Transmembrane Helices: The GxxxG Motif Occurs Frequently and in Association with Beta-Branched Residues at Neighboring Positions," *J. Mol. Biol.* 296:921-936.

Sharp et al. (2001) "Biochemical and Anatomical Evidence for Specialized Voltage Dependent Calcium Channel Gamma Isoform Expression in the Epileptic and Ataxic Mouse, Stargazer," *Neurosci.* 105(3):599-617.

Singer et al. (1991) "The Roles of the Subunits in the Function of the Calcium Channel," *Science* 253(5027):1553-1557.

Sitte et al. (Oct. 31, 2003) "Oligomer formation by $Na^+$—$CI^-$-coupled neurotransmitter transporters," *Eur. J. Pharmacol.* 479(1-3):229-236.

Soto et al. (Mar. 2009) "Selective Regulation of Long-Form Calcium-Permeable AMPA Receptors by an Atypical TARP, Gamma-5," *Nat. Neurosci.* 12(3):277-285.

Takebayashi et al. (2006) "Remodeling Excitation-Contraction Coupling of Hypertrophied Ventricular Myocytes is Dependent on T-type Calcium Channels Expression," *Biochem. Biophys. Res. Commun.* 345:766-773.

Tomita et al. (2003) "Functional Studies and Distribution Define a Family of Transmembrane AMPA Receptor Regulatory Proteins," *J. Cell. Biol.* 161:805-816.

Tomita et al. (2005) "Stargazin Modulates AMPA Receptor Gating and Trafficking by Distinct Domains," *Nature* 435:1052-1058.

Van Petegem et al. (2004) "Structure of a Complex Between a Voltage0Gated Calcium Channel Beta-Subunit and an Alpha-Subunit Domain," *Nature* 429:671-675.

Vandenberghe et al. (2005) "Stargazin is an AMPA Receptor Auxiliary Subunit," *Proc. Nat. Acad. Sci. USA* 102(2):485-490.

Vassort et al. (2006) "Role of T-type Ca2+ Channels in the Heart," *Cell. Calcium.* 40:205-220.

VMD Visual Molecular Dynamics, Webpage Document, Theoretical and Computational Biophys Group, University of Illinois at Urbana-Champaign, NIH Resource for Macromolecular Modeling and Bioinformatics; [online], Aug. 2005 [Retrieved on Sep. 29, 2005]. Retrieved from the Internet: URL: http://www.ks.uiuc.edu/Research/vmd/.

Wagner et al. (2004) "An Arginine Involved in GABA Binding and Unbinding but Not Gating of the GABA(A) Receptor," *J. Neurosci.* 24(11):2733-2741.

Wei et al. (1991) "Heterologous Regulation of the Cardiac Ca2+ Channel Alpha 1 Subunit by Skeletal Muscle Beta and Gamma Subunits. Implications for the Structure of Cardiac L-Type Ca2+ Channels," *J. Biol. Chem.* 266(32):21943-21947.

Williams et al. (1992) "Structure and Functional Expression of Alpha 1, Alpha2, and Beta Subunits of a Novel Human Neuronal Calcium Channel Subtype," *Neuron* 8(1):71-84.

Witschas et al. (2008) "3125-Pos Gamma6-Subunit Modulates Gating and Pharmacology of T-Type Calcium Channels," *Biophys. J.* Meeting Abstracts, Poster No. 3125, p. 1046, Feb. 2008.

Xu et al. (1990) "Increase in T-Type Calcium Current in Atrial Myocytes from Adult Rats with Growth Hormone-Secreting Tumors," *Proc. Nat. Acad. Sci. USA* 87:4655-4659.

Xu et al. (1992) "Postnatal Changes in T-Type Calcium Current Density in Rat Atrial Myocytes," *J. Physiol.* 454:657-672.

Zhang et al. (2002) "Mutations in High Voltage Activate Calcium Genes Stimulate Low Voltage Activated Currents in Mouse Thalamic Relay Neurons," *J. Neurosci.* 22:6362-6371.

Zhou et al. (2000) "Interhelical Hydrogen Binding Drives Strong Interactions in Membrane Proteins," *Nat. Struct. Biol.* 7(2):154-160.

E

F

SEQUENCE LISTING

<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Leu Gly Leu Leu Val Ala Ile Val
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic construct

<400> SEQUENCE: 2

Val Gly Leu Phe Phe Ala Leu Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic construct

<400> SEQUENCE: 3

Leu Gly Leu Leu Phe Ala Phe Val
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic construct

<400> SEQUENCE: 4

Phe Gly Phe Leu Val Ala Ile Val
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic construct

<400> SEQUENCE: 5

Leu Thr Leu Leu Val Ala Ile Val
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Val Gly Leu Thr Leu Ala Val Leu

<210> SEQ ID NO 7
<211> LENGTH: 8
<212> TYPE: PRT
<213> ORGANISM: Artificial Sequence
<220> FEATURE:
<223> OTHER INFORMATION: Synthetic construct

<400> SEQUENCE: 7

Val Gly Ala Thr Leu Ala Val Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Val Thr Leu Phe Phe Ile Leu Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic construct

<400> SEQUENCE: 9

Leu Leu Ile Leu Ala Val Gly Val
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Leu Thr Thr Ala Gly Ala Phe Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X1 is a hydrophobic aliphatic amino acid or
      phenylalanine
<220> FEATURE:
<221> NAME/KEY: MISC_FEATURE
<222> LOCATION: (2)..(2)
<223> OTHER INFORMATION: X2 is a small non-polar amino acid, serine, or
      threonine
<220> FEATURE:
<221> NAME/KEY: MISC_FEATURE
<222> LOCATION: (3)..(3)
<223> OTHER INFORMATION: X3 is aliphatic or phenylalanine
<220> FEATURE:
<221> NAME/KEY: MISC_FEATURE
<222> LOCATION: (4)..(4)
<223> OTHER INFORMATION: X4 is aliphatic, phenylalanine, or threonine
<220> FEATURE:

-continued

```
<221> NAME/KEY: MISC_FEATURE
<222> LOCATION: (5)..(5)
<223> OTHER INFORMATION: X5 is aliphatic or phenylalanine
<220> FEATURE:
<221> NAME/KEY: MISC_FEATURE
<222> LOCATION: (6)..(6)
<223> OTHER INFORMATION: X6 is a small non-polar amino acid
<220> FEATURE:
<221> NAME/KEY: MISC_FEATURE
<222> LOCATION: (7)..(7)
<223> OTHER INFORMATION: X7 is a hydrophobic aliphatic amino acid or
      phenylalanine
<220> FEATURE:
<221> NAME/KEY: MISC_FEATURE
<222> LOCATION: (8)..(8)
<223> OTHER INFORMATION: X8 is a hydrophobic aliphatic amino acid or
      phenylalanine

<400> SEQUENCE: 11

Xaa Xaa Xaa Xaa Xaa Xaa Xaa Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X1 is G or A or S
<220> FEATURE:
<221> NAME/KEY: MISC_FEATURE
<222> LOCATION: (2)..(2)
<223> OTHER INFORMATION: X2 is any amino acid
<220> FEATURE:
<221> NAME/KEY: MISC_FEATURE
<222> LOCATION: (3)..(3)
<223> OTHER INFORMATION: X3 is any amino acid
<220> FEATURE:
<221> NAME/KEY: MISC_FEATURE
<222> LOCATION: (4)..(4)
<223> OTHER INFORMATION: X4 is any amino acid
<220> FEATURE:
<221> NAME/KEY: MISC_FEATURE
<222> LOCATION: (5)..(5)
<223> OTHER INFORMATION: X5 is G or A or S

<400> SEQUENCE: 12

Xaa Xaa Xaa Xaa Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(4)
<223> OTHER INFORMATION: X independently is any amino acid

<400> SEQUENCE: 13

Gly Xaa Xaa Xaa Ala
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (2)..(4)
<223> OTHER INFORMATION: X independently is any amino acid

<400> SEQUENCE: 14

Gly Xaa Xaa Xaa Gly
1               5
```

US 8,299,211 B2

PEPTIDES AND REGULATION OF CALCIUM CHANNELS

CROSS-REFERENCES TO RELATED APPLICATIONS

This application claims the benefit of Application Ser. U.S. 61/047,929 by Best et al., filed Apr. 25, 2008; and is a continuation-in-part of application Ser. U.S. Ser. No. 11/537,323 by Best et al., filed Sep. 29, 2006, which claims the benefit of Application Ser. U.S. 60/722,707 by Best et al., filed Sep. 30, 2005, all of which are incorporated herein by reference in entirety.

STATEMENT ON FEDERALLY SPONSORED RESEARCH OR DEVELOPMENT

Not applicable

BACKGROUND OF THE INVENTION

Voltage-dependent calcium channels (VDCCs) control the gateways of calcium influx via the plasma membrane and thereby play essential roles in numerous biological activities such as synaptic transmission, muscle contraction, gene expression, hormone secretion, cell motility and development. Structurally, VDCCs comprise a pore-forming β subunit and as many as three auxiliary subunits: $β_2δ$, β and γ. The auxiliary β and $α_2δ$ subunits serve as positive regulators of calcium current by promoting surface expression of the $α_1$ subunit, enhancing voltage-dependent activation and increasing channel open probability. From recent work as set forth in this present disclosure, we have expanded the knowledge of the functions of the γ proteins as calcium channel auxiliary subunits, particularly in the context of the regulation of calcium channels. We also describe a further understanding of the mechanistic details.

The calcium channel γ family is a subgroup of tetraspanin proteins, which have four transmembrane segments and intracellular N- and C-termini. Among the eight γ subunits that have been identified, $γ_1$ was found in the calcium channel complex in skeletal muscles. Using $γ_1$-null mouse as an experimental model, $γ_1$ has been shown to accelerate voltage-dependent inactivation and reduce current density of the Cav1.1 channel in the skeletal muscles. Thus the function of the $γ_1$ subunit seems to be a negative regulator of the high voltage-activated (HVA) calcium current. There is indication that $γ_1$ interacts with the $α_{1.1}$ subunit through the first half of the γ molecule.

Despite the observation of the modulation or inhibition of HVA calcium currents by $γ_2$, $γ_3$, $γ_4$ and $γ_7$ in heterologous expression systems, certain attempts to demonstrate the influence of several γ subunits on HVA calcium current under physiological contexts (such as in neurons) have not been successful. Moreover, four of the eight subunits ($γ_2$, $γ_3$, $γ_4$ and $γ_8$) that contain a PDZ-binding motif in their C-termini have been recently found to act primarily as regulators of AMPA receptors and collectively named the transmembrane AMPA receptor regulatory proteins (TARPs). The gamma5 ($γ_5$) and gamma7 ($γ_7$) subunits have been proposed to act as type II TARPs that modulate glutamate receptor channels. Taken together, the biological roles of $γ_2$, $γ_3$, $γ_4$, $γ_5$, $γ_7$ and $γ_8$ as auxiliary subunits of calcium channels remain a subject of debate.

In contrast, $γ_6$, which is structurally the closest homologue of $γ_1$, is the only other γ subunit that seems to conform to the classical definition of a calcium channel subunit. In a heterologous expression system, $γ_6$ has been shown to robustly inhibit the calcium current of Cav3.1, a low voltage-activated (LVA) channel. In International Publication No. WO/2007/041360 and Patent Application Publication No. US 20070213267, we demonstrated that $γ_6$ not only associates with the $α_1$ subunit of the Cav3.1 channel, or the $α_{3.1}$ subunit, but also reduces LVA current density. We also identified a GxxxA motif in the first transmembrane domain (TM1) of $γ_6$ as critical for inhibiting the Cav3.1 current.

There is still a need in the art, however, for additional innovations and improvements towards the ability to generate relatively short peptides which are active in regulating calcium channel function. Moreover, the earlier characterization of the structure of useful peptides is further advanced by the present disclosure. We identify structural features of peptides, particularly short peptides capable of demonstrating significant activity levels in affecting calcium channel function, which facilitate the generation of compositions and methods including pharmacologic agents and therapeutic applications. Embodiments of the present invention therefore address such need.

SUMMARY OF THE INVENTION

The invention at least in part relates to embodiments of protein and peptide compositions and methods capable of regulating calcium channel function.

Embodiments of the invention provide and demonstrate compositions of proteins and relatively short peptides. Embodiments also include methods of applying such compositions for regulation of calcium channel function, including in the context of modulating calcium current in mammalian cells. Embodiments of compositions can be active for LVA and HVA calcium channel function. In certain embodiments we have shown that peptides of the invention are able to block ionic current, particularly Cav3.1 current. Peptide compositions preferably include a GxxxA motif with certain nearby residues having aliphatic side chains. Peptide compositions include such having the GxxxA motif from γ6 TM1 with an overall length of from five to 14 amino acids. Other preferred peptides have a length of six to 10 amino acids, and particularly preferred peptides have a length of eight amino acids.

In an embodiment, the invention provides an isolated peptide having a sequence of X1-X2-X3-X4-X5-X6-X7-X8 (SEQ ID NO: 11); wherein X1 is a hydrophobic aliphatic amino acid or phenylalanine; X2 is a small non-polar amino acid, serine, or threonine; X3 is aliphatic or phenylalanine; X4 is aliphatic, phenylalanine, or threonine; X5 is aliphatic or phenylalanine; X6 is a small non-polar amino acid; and each X7 and X8 independently is a hydrophobic aliphatic amino acid or phenylalanine.

In an embodiment, X1 is L, I, V, or F; X2 is G, A, S, or T; X3 is L, I, V, A, or F; X4 is L, I, V, A, F, or T; X5 is L, I, V, A, or F; X6 is G, A, or S; and each X7 and X8 independently is L, I, V, A, or F. In an embodiment, X1 is L, V, or F; X2 is G; at least two of X3, X4, and X5 are L, V, or F; and X6 is A. In an embodiment, if X2 is other than G, X6 is G or A. In an embodiment, X2 is G; X6 is A; and four of X1, X3, X4, X5, X7, and X8 are L, V, or F.

In an embodiment, the invention provides a peptide having a sequence of: SEQ ID NO:1, gamma6 TM1a; SEQ ID NO: 2, gamma1 TM1a T12GI16A; SEQ ID NO:3, gamma6 TM1a V45FI47F; SEQ ID NO:4, gamma6 TM1a L41 FL43F; SEQ ID NO:5, gamma6 TM1a G42T; SEQ ID NO:6, gamma6 TM1b A50L; or SEQ ID NO:7, gamma6 TM1b.

In an embodiment, the invention provides a peptide wherein X1, X7, and X8 are 0 (absent) and said peptide consists of 5 to 14 amino acids. In an embodiment, a peptide has a peptide length of 6, 7, 8, 9, 10, 11, 12, 13, or 14 amino acids. In an embodiment, a peptide has a length of eight amino acids.

In an embodiment of a peptide, two of X1, X7, and X8 are 0 (absent) and said peptide consists of 6, 7, 8, 9, 10, 11, or 12 amino acids. In an embodiment, one of X1, X7, and X8 are 0 and said peptide consists of 7, 8, 9, 10, 11, or 12 amino acids. In an embodiment, each of X3, X4, and X5 independently is an aliphatic amino acid.

In an embodiment, the invention provides a peptide having an amino acid sequence homology percentage of at least 80, 85, 90, 91, 92, 93, 94, 95, 96, 97, 98, or 99% identity to a peptide of the invention described herein.

In an embodiment, the invention provides a nucleic acid molecule encoding a peptide of the invention.

In an embodiment, the invention provides a method of regulating a calcium channel comprising contacting said calcium channel with a peptide of the invention. In an embodiment, the calcium channel is a voltage dependent calcium channel. In an embodiment, the calcium channel is a low voltage-activated calcium channel. In an embodiment, the calcium channel is a high voltage-activated calcium channel. In an embodiment, the calcium channel is a Cav3.1 channel. In an embodiment, the regulating inhibits calcium current. In an embodiment, the regulating is selective for a low voltage-activated channel.

In an embodiment, compositions and methods are useful in selectively regulating an HVA channel.

In an embodiment, a composition is capable of regulating the function of at least one type of calcium channel, e.g., Cav1, Cav2, or Cav3. In an embodiment, a composition selectively regulates all three calcium channel gene families, namely Cav1, Cav2, and Cav3.

In an embodiment, the calcium channel is in a mammalian cell. In an embodiment, the mammalian cell is a cell line, a cardiomyocyte, or a neuronal cell.

In an embodiment, the regulating is at least partially reversible.

In an embodiment, the invention provides a method of modifying multimerization or a helix-helix protein domain interaction of a protein containing a GXXXA motif, comprising contacting said protein with a peptide of the invention.

In an embodiment, the invention provides a pharmaceutical composition comprising as an active ingredient an effective amount of a peptide of the invention. In an embodiment, the pharmaceutical composition further comprises a pharmaceutically acceptable carrier.

In an embodiment, the invention provides a method of treating a disorder of calcium channel regulation comprising administering to a patient in need thereof a therapeutically effective amount of a peptide of the invention or a pharmaceutical composition thereof. In an embodiment, the disorder is a cardiomyopathy, cardiac arrhythmia, or cardiac hypertrophy. In an embodiment, the disorder is a neurological disorder. In an embodiment, the disorder is an epileptic disorder; in a particular embodiment, the disorder is a neural epilepsy. In an embodiment, the neurological disorder is an anxiety disorder. In an embodiment, the disorder is cellular hypertrophy.

In an embodiment, the invention provides a method of treating a disorder comprising administering to a patient in need thereof a therapeutically effective amount of a peptide of the invention or a pharmaceutical composition thereof.

In embodiments, the invention provides methods of modifying protein interaction such as multimerization, including dimerization, or interhelical interaction between protein domains. In embodiments, the invention inhibits multimerization of transmembrane helical domains in membrane proteins.

In embodiments, protein and peptide compositions are generated which have a GxxxA motif and nearby amino acid residues with aliphatic and preferably beta branching side chains.

In an embodiment of regulation of calcium current, the regulation is at least partially reversible. In an embodiment, the regulation of calcium channel function is an inhibition of calcium current.

In embodiments, compositions of the invention are applied to mammalian cells extracellularly.

In an embodiment, the invention provides a pharmaceutical composition, such as a pharmaceutical formulation, comprising a composition of the invention. In an embodiment, the invention provides a method of synthesizing a composition of the invention or a pharmaceutical composition. In an embodiment, a pharmaceutical composition comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention; 2007; and 2008, and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, a formulation base of the formulations of the present invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

Variations on compositions including salts and ester forms of compounds: Compounds of this invention and compounds useful in the methods of this invention include those of the compounds and formula(s) described herein and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds of the names and structural formulas herein. In embodiments, salts and esters of the compounds of the formulas herein can include those which have the same or better therapeutic or pharmaceutical (human or veterinary) general properties as the compounds of the formulas herein. In an embodiment, a composition of the invention is a compound or salt or ester thereof suitable for pharmaceutical compositions.

In an embodiment, an effective amount of a composition of the invention can be a therapeutically effective amount. In an embodiment, an active ingredient or other component is included in a therapeutically acceptable amount. In an embodiment, the invention provides a method for treating a medical condition comprising administering to a subject in need thereof, a therapeutically effective amount of a composition of the invention. In an embodiment, the invention provides a medicament which comprises a therapeutically effective amount of one or more compositions of the invention. In an embodiment, the invention provides a medicament which comprises a diagnostically effective amount of one or more compositions of the invention. In an embodiment, the invention provides a method for making a medicament for treatment of a condition described herein. In an embodiment, the invention provides a method for making a medicament for diagnosis or aiding in the diagnosis of a condition described herein. In an embodiment, the invention provides the use of one or more compositions set forth herein for the making of a medicament.

In an embodiment, a composition of the invention is isolated or purified. In an embodiment, the status of being isolated or purified is in the context as would be understood in the relevant field of art. The degree of isolation or purification can be partial and is not necessarily at the level of complete homogeneity.

In an embodiment, a composition of the invention is a peptide compound. In an embodiment, a composition of the invention is a nucleic acid compound. In an embodiment, a composition of the invention is a nucleic acid capable of encoding a peptide as understood in the art.

In an embodiment, the invention provides a pharmaceutical formulation comprising a composition of the invention. In an embodiment, the invention provides a method of synthesizing a composition of the invention or a pharmaceutical formulation thereof. In an embodiment, a pharmaceutical formulation comprises one or more excipients, carriers, and/or other components as would be understood in the art. In an embodiment, an effective amount of a composition of the invention can be a therapeutically effective amount.

In an embodiment, a peptide composition of the invention is prepared using recombinant methodology or synthetic techniques. In an embodiment, a nucleic acid composition of the invention is prepared using recombinant methodology or synthetic techniques. In an embodiment, an amino acid residue can be a naturally proteinogenic amino acid. In an embodiment, a peptide composition can include one or more amino acid residues which can be naturally proteinogenic amino acids and/or one or more synthetic amino acids, which can optionally be non-proteinogenic amino acids or derivatives, wherein the composition is capable of effecting calcium channel regulation.

In an embodiment, the invention provides a medicament which comprises a therapeutically effective amount of one or more compositions of the invention. In an embodiment, the invention provides a method for making a medicament for treatment of a condition described herein.

As pertaining to certain embodiments, our understanding of the mechanism generally is that an active peptide inhibits the Cav3.1 current by dynamically binding and dissociating from the Cav3.1 channel in a concentration dependent, but largely voltage independent manner. By generating a number of variants of peptide sequences, we identified residues of the peptide structure which are compatible with function. We generally showed that both the GxxxA motif framework and surrounding aliphatic side-chains can contribute to the presumably inter-helical interactions between γ6 TM1 and the native Cav3.1 channel. The fast kinetics of the interaction supports a mechanistic view where γ6, thus peptide derivatives thereof also, modulates the Cav3.1 channel directly within the plasma membrane. In this view, the mechanism is not dependent of surface expression or membrane trafficking of the pore-forming subunit of the channel. In addition to contributing to fundamental understandings of the underlying mechanism of the channel function, useful compositions and methods are set forth such as therapeutic agents for conditions and disorders relating to calcium channel function and regulation.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

DETAILED DESCRIPTION OF THE INVENTION

Figure 1:
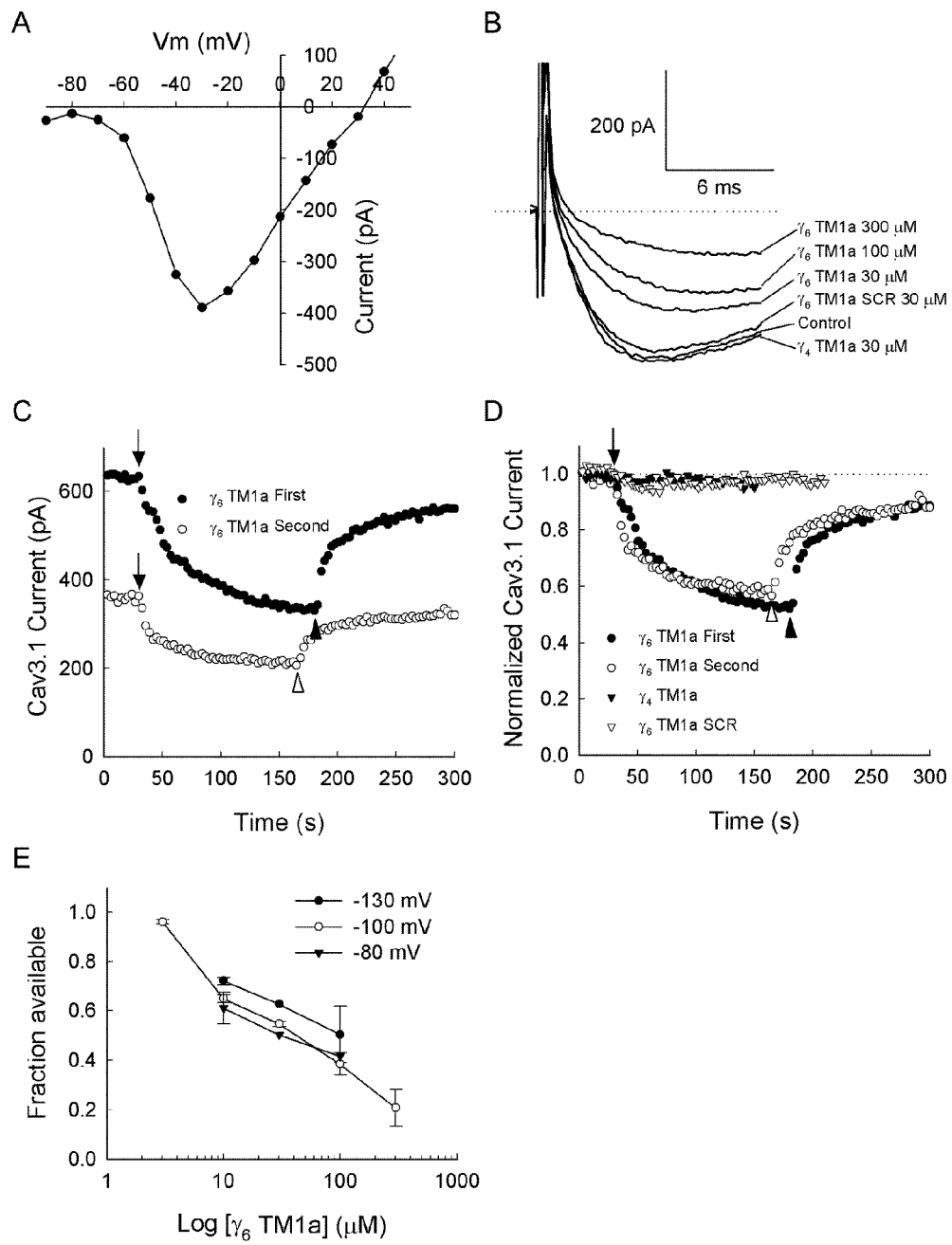
FIG. 1 illustrates graphic data from testing short peptides including γ6 TM1a and other peptides for activity in regulating calcium channel function. (A) Cav3.1 current-voltage (I-V) relationship from a typical HEK/Cav3.1 cell. (B) A representative cell showing the steady-state current amplitude of Cav3.1 currents in the presence of various peptides. (C) Time course of Cav3.1 current inhibited by 30 µM $\gamma_6$ TM1a in a representative cell. (D) Normalized time course data. (E) Dose- and voltage-dependency of α3.1-$\gamma_6$ TM1a interaction.
Figure 1:
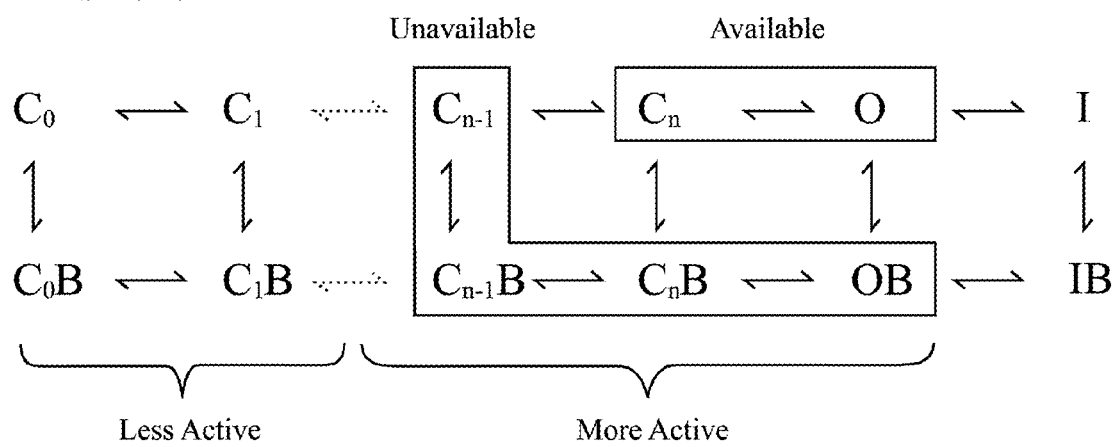

The following abbreviations may be used: α, alpha; β, beta; δ, delta; γ, gamma; τ, tau; LVA, low voltage-activated; TM, transmembrane; Cav, Calcium current regulated by voltage; V0.5, half-maximal potentials; VDCC, voltage-dependent calcium channel; HVA, high voltage-activated; LVA, low voltage-activated; PDZ, PSD-95/DLG/ZO-1; AMPA, α-amino-3-hydroxy-5-methylisoxazole-4-propionic acid; TARP, transmembrane AMPA-receptor regulatory protein.

In general the terms and phrases used herein have their art-recognized meaning, which can be found by reference to standard texts, journal references and contexts known to those skilled in the art and particularly in the field of the art. The following definitions are provided to clarify their specific use in the context of embodiments of the invention.

GxxxA and GXXXG-like motifs. When used herein, the term refers to a peptide structural motif that has an initial and a terminal amino acid wherein each independently has a small side chain. Examples of amino acids with small side chains include glycine (G), alanine (A), and serine (S). The term 'GxxxA motif' is intended to be equivalent to a GXXXG-like motif. In particular embodiments, the motif refers to a peptide motif having a sequence of (G or A or S)XXX(G or A or S) (SEQ ID NO:12), wherein each X is independently any amino acid. In a particular embodiment, the motif is a motif naturally found in a mammalian species in a γ6 calcium channel protein, more particular such motif of a γ6 TM1a peptide segment, or a derivative thereof. A particular example of a GxxxG-like motif or GxxxA motif is GxxxA (SEQ ID NO:13). Another example is GxxxG (SEQ ID NO:14).

Cav. When used herein, the term refers to voltage dependent calcium channels. Particular designations are presented in the conventional format: $Ca_vZZ$, for example, Cav3.1, to indicate gene names for alpha1 subunits of voltage dependent calcium channels.

The invention may be further understood by the following non-limiting examples.

EXAMPLE 1

The calcium channel γ6 subunit regulates calcium channel function by modulating low voltage-activated (LVA) calcium current in mammalian cells such as cardiomyocytes. We have previously disclosed that γ6 contains a critical peptide sequence motif in the first transmembrane domain (TM1) that is essential for inhibition of the calcium current, for example in the context of Cav3.1, an LVA channel.

Overview. We hypothesized that a short, GxxxA motif-containing peptide from $\gamma_6$ TM1 is sufficient to bind directly to and block the Cav3.1 current like a pharmacological agent. In addition, we refined the sequence context of the peptide by performing a variety of substitutions of residues within the central motif and surrounding residues. We identified structural features which facilitate the generation of peptide compositions and methods for regulating calcium channel function.

From a mechanistic view, the results indicate that the binding of native $\gamma_6$ TM1a peptide, and therefore certain peptide embodiments of the invention, to the Cav3.1 channel is dose-dependent, but not voltage-dependent. This binding is mediated in part by the aliphatic side chains of residues surrounding a central GxxxA motif. It is believed that $\gamma_6$ can modulate Cav3.1 current by directly blocking calcium flux through the $\alpha_{3.1}$ subunit on the plasma membrane, a mechanism that is independent of alteration of surface expression (i.e. trafficking) of the $\alpha_{3.1}$ subunit. There is also a slower component of current decrease that is interpreted to possibly be due to a change in channel number at the membrane.

The data also demonstrates that certain peptide embodiments, such as the $\gamma_6$ TM1a peptide, inhibited Cav1.2 current less effectively as it did Cav3.1 current. Therefore embodiments of peptide compositions and methods are provided which selectively modulate LVA preferentially rather than HVA currents under physiological conditions.

Materials and Methods

Cell Culture. HEK 293 cell lines used in this study were gifts from Professor Dottie Hank at the University of Chicago. A HEK cell line stably expressing the Cav3.1 current was maintained at 37° C. in Dulbecco's modified Eagles medium (DMEM, Cell Media Facility, School of Chemical Sciences, University of Illinois at Urbana-Champaign) with 10% FBS (Invitrogen, Carlsbad, Calif.), 1% penicillin/streptomycin and 50 μg/mL Hygromycin B in 5% $CO_2$. Another HEK cell line expressing stable β2a and inducible Cav1.2 current was maintained in the same condition, except for that its medium contains DMEM with 10% FBS, 1% penicillin/streptomycin, 200 μg/ml Geneticin, 15 μg/ml Blasticidin, and 50 μg/ml Hygromycin B. Forty-eight (48) hr before recording, 2 μg/ml of tetracycline was added to the medium to turn on the expression of Cav1.2 gene. For recordings, cells were plated on cover slips in 35 mm culture dishes.

Peptides. A series of 8-amino acid peptides based on TM1 of $\gamma_1$, $\gamma_4$ or $\gamma_6$ were designed and ordered from a commercial source, EZBiolab Inc. (Westfield, Ind.) and dissolved as 50 or 100 mM stocks in dimethylsulfoxide (DMSO). From the DMSO stocks the peptides were then diluted into recording solutions to a final concentration of 3 to 300 μM. The highest DMSO concentration in peptide-containing solutions was 85.2 mM (in 300 μM $\gamma_6$ TM1a, see results section), and was found to have no effect on calcium current alone. Most of the peptides were tested at 30 μM unless otherwise noted. The names and sequences of the peptides used in this study are as following: γ6 TM1a (LGLLVAIV); γ6 TM1a SCR (LLILAVGV); γ4 TM1a (LTTAGAFA); γ6 TM1a G42T (LTLLVAIV); γ6 TM1a L41 FL43F (FGFLVAIV); γ6 TM1a V45FI47F (LGLLFAFV); γ6 TM1b (VGATLAVL); γ6 TM1b A50L (VGLTLAVL); γ1 TM1a (VTLFFILA); γ1 TM1a T12GI16A (VGLFFALA).

Electrophysiology. Whole cell $Ca^{2+}$ currents were recorded using an Axopatch-1D amplifier and Clampex 8.2 software (Molecular Devices, Sunnyvale, Calif.) at room temperature (~25° C.). Pipettes were fabricated from borosilicate glass and had typical resistances of 2-4 MΩ. The pipette solution contained (in mM) 87 NaCl, 50 CsF, 10 EGTA, 3.3 $MgCl_2$, 0.67 $CaCl_2$ and 10 HEPES. The bath solution for recording Cav3.1 current contained (in mM) 137 NaCl, 5.4 KCl, 2 $CaCl_2$, 1 $MgCl_2$, 0.33 $NaH_2PO_4$ and 10 HEPES. The bath solution for recording Cav1.2 current contained (in mM) 125 CsCl, 10 $BaCl_2$, 2 $MgCl_2$ and 10 HEPES. All solutions were adjusted to pH 7.4 and 290 mOsm (with sucrose).

Liquid junction potentials were corrected before seals of pipettes with cells were obtained in bath solutions. The pipette resistance and capacitance were then electronically cancelled. Upon breaking into the cell, the cell capacitance and access resistance were estimated by a membrane test routine. Whole cell capacitance was compensated while series resistance was not compensated because most of peak currents were smaller than 500 pA with access resistance less than 7 MΩ (voltage error <3.5 mV). Once the whole-cell configuration is formed, the cell was then lifted and moved in front of an array of sewer pipes (microcapillary from Drummond; content 1 μl, length 64 mm) emitting either control or peptide-containing recording solutions. The calcium currents were elicited at −30 mV every 3 s (for Cav3.1) or 0 mV every 5 s (for Cav1.2) from a holding potential of −100 mV unless otherwise noted. To estimate the potency of each peptide, steady-state current amplitude in a peptide solution was normalized to the current amplitude of the same cell during the test pulse in the control solution immediately before the cell was moved into that peptide solution.

Data were digitized at 10-20 kHz and filtered at 2 kHz. All data are reported as means±standard error of mean (S.E.M). Statistically significant levels were tested using single factor ANOVA. A p-value of 0.05 was considered significant when using the Tukey's multiple comparison test. Significant levels are expressed as *$p<0.05$, $p<0.01$, and *$p<0.001$.

Results

Several peptides were generated and tested. See Table 1.

TABLE 1

Peptides and sequence listing information.

| SEQ ID NO: | Peptide ID | Sequence, amino acids |
|---|---|---|
| 1 | γ6 TM1a | LGLLVAIV |
| 2 | γ1 TM1a T12GI16A | VGLFFALA |
| 3 | γ6 TM1a V45FI47F | LGLLFAFV |
| 4 | γ6 TM1a L41FL43F | FGFLVAIV |
| 5 | γ6 TM1a G42T | LTLLVAIV |
| 6 | γ6 TM1a A50L | VGLTLAVL |
| 7 | γ6 TM1b | VGATLAVL |
| 8 | γ1 TM1a | VTLFFILA |
| 9 | γ6 TM1a SCR | LLILAVGV |
| 10 | γ4 TM1a | LTTAGAFA |

$\gamma_6$ TM1a 8mer peptide acts as a pharmacological agent to block Cav3.1 current. Cav3.1 currents from our HEK cells displayed fast activation and inactivation that are typical of LVA calcium current. The current-voltage relationship (FIG. 1A) peaked around −30 mV, which was the testing voltage used for evaluating the efficacy of all of the peptides on Cav3.1 current. We first tested the peptide $\gamma_6$ TM1a (from the first half of $\gamma_6$ TM1), which contains residues 41 through 48 of the native $\gamma_6$ protein and a GxxxA motif in the center. When we applied $\gamma_6$ TM1a at various concentrations, the blockade of the Cav3.1 current is apparently dose-dependent (FIG. 1B).

By moving the cell relative to the sewer pipe array the solution around the cell can be completely changed within a time of 200-400 ms. This allowed observation of the relatively slow process of binding and unbinding between various peptides and $\alpha_{3.1}$, or the $\alpha_1$ subunit of the Cav3.1 channel. As shown in FIG. 1C, the Cav3.1 current was progressively inhibited by $\gamma_6$ TM1a after being exposed to 30 μM of the peptide solution (time of administration indicated by arrows). Upon removal of the peptide (by switching the cell back to the control solution, indicated by arrowheads), the calcium current recovered from ~55% to ~88% of its control level, indicating that ~73% of the inhibition was reversible. In all of the cells tested against $\gamma_6$ TM1a, a certain portion of the current never recovered. Therefore the $\gamma_6$ TM1a-α3.1 binding can feature both reversible and irreversible fractions. We also found that the irreversible portion does not affect the binding process upon the next exposure to the same solution. When calcium currents are normalized to the last current amplitude immediately before switching into the peptide solution, both exposures resulted in nearly identical time courses (FIG. 1D). This allowed us to test multiple peptides at various dosages on a single cell without having to factor a confounding effect from previous peptide exposure. From the same cell, we also found that a peptide from $\gamma_4$ TM1 ($\gamma_4$ TM1a) or a scrambled version of $\gamma_6$ TM1a ($\gamma_6$ TM1a SCR) had no effect on Cav3.1 current. Therefore the 8mer peptide of $\gamma_6$ TM1a has structural features distinct from non-active peptides such as other 8mer peptides.

To examine the dose and voltage dependence of the blockade of the Cav3.1 current by $\gamma_6$ TM1a, a concentration range of 3 to 300 μM $\gamma_6$ TM1a was used to assay the extent of current inhibition under −80, −100 or −130 mV holding potentials. As can be seen in FIG. 1E, $\gamma_6$ TM1a inhibits Cav3.1 current in a dose-dependent fashion. However, there is very little voltage dependence for the binding between $\gamma_6$ TM1a and Cav3.1 channel, as the three curves in FIG. 1E have virtually the same slope.

Analysis of the kinetics of $\gamma_6$ TM1a-$\alpha_{3.1}$ binding further illustrated the dose-dependent nature of the interaction. In our view, the kinetics are similar to certain drug-receptor interactions. When the binding interaction was characterized by fitting the time courses of current inhibition (as in FIG. 1D) with bi-exponential curves, the dominant component ($A_{fast}$) displayed a strong correlation with the concentration of $\gamma_6$ TM1a (FIG. 2A) and accounted for the extent of current inhibition shown in FIG. 1E. On the other hand, the minor component ($A_{slow}$) accounted for less than 10% of the current amplitude and had no apparent correlation with the peptide concentration. When the time constant of the dominant component ($\tau_{fast}$) was plotted against $\gamma_6$ TM1a concentration, a dose-dependent decrease of the time constant was also observed (FIG. 2B). The unbinding process, fitted with bi-exponential components from the relaxation of Cav3.1 current upon removing the $\gamma_6$ TM1a peptide (as in FIG. 1D), also revealed the drug-like nature of $\gamma_6$ TM1a. The dominant (and fast) component of the unbinding process displayed a correlation with concentration. The Cav3.1 current recovered the most from exposure to 300 μM ($A_{fast}$=−0.37±0.05 in FIG. 2C), in which the Cav3.1 was mostly inhibited (79.3±7.5%, FIG. 1E). The time constant of the unbinding process is not concentration-dependent, as this process occurred in the control solution (FIG. 2D).

GxxxA motif and surrounding residues determine the efficacy of the Cav3.1 current inhibition. FIG. 3A shows the summarized effects of three peptides on the Cav3.1 current at 30 μM. In contrast to $\gamma_6$ TM1a, which inhibited the Cav3.1 current by 45.3±1.0%, γ4 TM1a and $\gamma_6$ TM1a SCR caused no inhibitory effects (−3.5±2.7% and 0.5±2.9%, respectively). This result indicates that the inhibition of the Cav3.1 current by $\gamma_6$ TM1a is sequence-specific. We proceeded to further delineate significant attributes of the sequence specificity which correlate with functional activity.

The GxxxA motif in $\gamma_6$ TM1a conforms to a general definition of the (G or A or S)xxx(G or A or S) motif that forms the framework of interhelical interactions of many soluble and membrane associated proteins. For embodiments of the invention, in addition to the central (G1A/S)xxx(G1A/S) motif, the neighboring residues such as aliphatic residues (V, I, L) at adjoining (±1) positions also provide essential stability and flexibility for the helix/helix interaction. In this context, the +1 and −1 positions are designated relative to the G or A of the GxxxA motif; thus −1 is before the G (glycine) and +1 is after the G, and likewise for the A (alanine). In an alternative designation system, the amino acid residues and relative peptide positions are indicated by $X_n$, where X independently is an amino acid and subscript n is a number for the relative position in the conventional order of direction, proceeding from the N-terminus towards the C-terminus of a protein molecule.

To further explore the sequence context that mediates the $\gamma_6$ TM1a-$\alpha_{3.1}$ interaction and contributes to functional efficacy, we designed, generated, and tested other 8-amino acid peptides containing mutated residues of $\gamma_6$ TM1a and sequences from $\gamma_6$ TM1b and $\gamma_1$ TM1a. Because certain of the peptides reported herein are relatively hydrophobic, in some instances there was difficulty in obtaining concentrations above 30 μM in the control solution. Therefore we generally applied all peptides at 30 μM.

We investigated aspects of the GxxxA motif first by substituting the glycine at position 42 of the $\gamma_6$ TM1a with leucine, an aliphatic residue. The mutant peptide ($\gamma_6$ TM1a G42L: LLLLVAIV) failed to be synthesized by the manufacturer, which was believed due to the highly hydrophobic nature. We then substituted the glycine with threonine, a polar residue. This substitution ($\gamma_6$ TM1a G42T) greatly enhanced the solubility of the peptide. At 30 μM of $\gamma_6$ TM1a G42T, this variant was active and inhibited the Cav3.1 current by 16.4±1.7%; however, the activity was statistically significantly less than the wild-type $\gamma_6$ TM1a (p<0.001, FIG. 3B). We next replaced the aliphatic residues at the adjoining positions of the GxxxA motif with phenylalanine, a hydrophobic but non-aliphatic residue. As shown in FIG. 3B, these substitutions yielded active peptides but also reduced the potencies of these peptides ($\gamma_6$ TM1a L41FL43F: 20.6±2.2%; $\gamma_6$ TM1a V45FI47F: 26.3±3.3%) relative to the $\gamma_6$ TM1a peptide. Taken together, these results indicate that both the GxxxA framework and its neighboring aliphatic residues are involved in the $\gamma_6$ TM1a-$\alpha_{3.1}$ interaction. Thus multiple active peptides are generated in addition to an understanding of structural features allowing for generation of further variants.

We further assessed the importance of the GxxxA motif. We tested a short peptide, $\gamma_1$ TM1a, which lacks the GxxxA motif. The $\gamma_1$ TM1a peptide is derived from the full-length $\gamma$ protein $\gamma_1$, which lacks a GxxxA motif in the first half of TM1. The short peptide, $\gamma_1$ TM1a, does not inhibit Cav3.1 current (current inhibition=2.4±2.2%, FIG. 3C). We positively introduced a GxxxA motif into a short peptide, designated $\gamma_1$ TM1a T12GI16A. Strikingly, $\gamma_1$ TM1a T12GI16A was a relatively potent inhibitor of calcium channel function (29.4±2.9%, FIG. 3C).

The second half of the $\gamma_6$ TM1 also contains a $G^{49}xxxA^{53}$ motif, but it is not implicated in the inhibition of the LVA Cav3.1 current by full length $\gamma_6$ (see WO/2007/041360). We sought to determine aspects of what can make the motif functional or not, particularly in the context of short peptides. We generated a short peptide, $\gamma_6$ TM1b, containing residues 48 through 55 of wild-type $\gamma_6$. When it was tested, $\gamma_6$ TM1b was active but produced very little (5.5±2.3%) inhibition on Cav3.1 current (FIG. 3D). Careful examination of the sequences of $\gamma_6$ TM1a and $\gamma_6$ TM1b revealed that $\gamma_6$ TM1b has an Ala50 in the adjoining position of Gly49, and Thr51 in the center of the GxxxA motif. Substituting the alanine with leucine, we generated another short peptide, $\gamma_6$ TM1b A50L; this peptide was active but only slightly increased the extent of current inhibition (15.8±2.2%) relative to $\gamma_6$ TM1b. Despite having a complete GxxxA motif surrounded by aliphatic residues, TM1b A50L is much less potent than $\gamma_6$ TM1a as a Cav3.1 current inhibitor (FIG. 3D), suggesting that the hydroxyl group from Thr51 could be disruptive for the $\gamma_6$-$\alpha_{3.1}$ interaction.

FIG. 3E shows the sequence and annotation of peptides ranked by their relative potency of inhibiting the Cav3.1 current at 30 μM. Peptides without a complete GxxxA motif ($\gamma_6$ TM1a SCR and $\gamma_1$ TM1a) are generally unable to interact and reduce the Cav3.1 current. A polar threonine in the center of a GxxxA motif ($\gamma_6$ TM1b, $\gamma_6$ TM1b A50L) can disrupt the helix/helix interaction and therefore affect the activity level. Hydrophobic interactions provided by aliphatic residues around the GxxxA framework ($\gamma_6$ TM1a, $\gamma_1$ TM1a T12GI16A) can facilitate enhanced binding between peptides and the Cav3.1 channel.

$\gamma_6$ TM1a peptide inhibits the Cav1.2 current with reduced efficacy. We performed a series of recordings on HEK 293 cells expressing tetracycline-inducible Cav1.2 currents. Illustrated in FIG. 4A are the long-lasting, non-inactivating barium currents through the Cav1.2 channel from a representative cell and its associated current-voltage relationship. When the time courses of current inhibition by various peptides were observed at 0 mV testing potential, it was again found that the $\gamma_6$ TM1a SCR produced no inhibition on the Cav1.2 current (FIG. 4B). A concentration of 30 μM of $\gamma_6$ TM1a caused a moderate Cav1.2 current inhibition (25.6±2.4%, FIGS. 4B and 4C), and only around 50% of the inhibition was reversible (cf. ~73% in Cav3.1 current, FIG. 1D). When the steady-state current amplitudes were normalized against control levels, it was again found that $\gamma_4$ TM1a and $\gamma_6$ TM1a SCR are not Cav1.2 current inhibitors (−2.5±1.8% and 3.2±0.8%, respectively), as shown in FIG. 4C. Consistent with the result on Cav3.1 current, $\gamma_6$ TM1b caused little inhibition of the Cav1.2 current (6.7±0.7%, FIG. 4D). $\gamma_1$ TM1a, although significantly less potent than $\gamma_6$ TM1a, surprisingly inhibited the Cav1.2 current by 15.5±2.0% (FIG. 4D). Introducing a GxxxA motif into $\gamma_1$ TM1a further enhanced the current inhibition by $\gamma_1$ TM1a T12GI16A to 27.5±3.3%, making it as potent as $\gamma_6$ TM1a in inhibiting the Cav1.2 current (FIG. 4D). Finally, when the various peptides were ranked by their efficacies in reducing Cav1.2 current (FIG. 4E; see also Table 2), it was apparent that a GxxxA framework and hydrophobic interactions are still significant for activity. Taken together, our results from the Cav1.2 current recordings indicated that $\gamma_6$ TM1a is capable of suppressing the Cav1.2 current through the Gxxxa motif and its surrounding hydrophobic residues. On the other hand, the extent of current inhibition produced by $\gamma_6$ TM1a is greater on the Cav3.1 than on the Cav1.2 current (cf. FIGS. 3E and 4E). Thus we demonstrate peptides which can be active in the context of LVA and HVA currents. Furthermore, certain peptides can be selective inhibitors for calcium currents, e.g., a peptide can preferentially inhibit LVA current versus HVA current.

TABLE 2

Peptide sequences with annotation.

| SEQ ID NO. | Peptide ID | Sequence |
| --- | --- | --- |
| 1 | γ6 TM1a | * * * *<br>LGLLVAIV |
| 2 | γ1 TM1a T12GI16A | *  *   *<br>VGLFFALA |
| 3 | γ6 TM1a v45FI47F | * *<br>LGLLFAFV |
| 4 | γ6 TM1a L41FL43F | * *<br>FGFLVAIV |
| 5 | γ6 TM1a G42T | * * * *<br>LTLLVAIV |
| 6 | γ6 TM1a A50L | * * * *<br>VGLTLAVL |
| 7 | γ6 TM1b | *  * *<br>VGATLAVL |
| 8 | γ1 TM1a | *  *  <br>VTLFFILA** |
| 9 | γ6 TM1a SCR | ****  * *<br>LLILAVGV |

TABLE 2-continued

Peptide sequences with annotation.

| SEQ ID NO. | Peptide ID | Sequence |
|---|---|---|
| 10 | γ4 TM1a | *<br>L*TTAGAFA* |

Legend * asterisk above, LARGE ALIPHATIC double underlined, SMALL NON-POLAR italic and underlined, POLAR In the above table, an asterisk above the character indicates a large aliphatic residue; a double underlined character indicates a small, non-polar residue; and a character which is in italics and underlined indicates a polar residue.

Discussion. GxxxA and surrounding aliphatic residues can determine $\gamma_6$-α3.1 interaction. We disclose that $\gamma_6$ TM1a, a GxxxA containing peptide from the first half of $\gamma_6$ TM1, can block the Cav3.1 current. Furthermore, from our results with other peptides from TM1 of $\gamma_6$, $\gamma_4$ or $\gamma_1$, we conclude that the GxxxA motif plays a pivoting role in the inhibition of the Cav3.1. We demonstrate that the efficacy of interaction between $\gamma_6$ TM1a and $\alpha_{3.1}$ is sequence-dependent and requires a GxxxA framework with certain surrounding aliphatic residues. Our substitution experiments showed that both the GxxxA framework and aliphatic residues (V, I, L) at the adjoining positions are involved in the $\gamma_6$-$\alpha_{3.1}$ interaction (FIG. 3B). This is also supported by the fact that introduction of a GxxxA motif into $\gamma_1$ TM1a converted a non-active peptide into a potent inhibitor (FIG. 3C).

Both van der Waals interaction and hydrogen bonding can mediate helix/helix packing. In the case of the $\gamma_6$-$\alpha_{3.1}$ interaction, our data from $\gamma_6$ TM1b and $\gamma_6$ TM1b A50L (FIG. 3D) suggest that the interaction is provided mainly by van der Waals interactions between hydrophobic residues, as the polar hydroxyl group from Thr51 appears to be disruptive to this interaction. By substituting aliphatic residues around the GxxxA motif with phenylalanine (FIG. 3B), we also showed that the $\gamma_6$-$\alpha_{3.1}$ interaction is indeed enhanced for aliphatic, rather than any hydrophobic residues.

When we tested various peptides on the Cav1.2 current, we similarly observed the importance of the GxxxA motif and a hydrophobic sequence context. However, the $\gamma_1$ TM1a T12GI16A is, if not more, as potent as $\gamma_6$ TM1a in terms of potency of HVA current inhibition (FIGS. 4D, 4E). It is noted that there are two consecutive phenylalanines in the core of $\gamma_1$ TM1a T12GI16A. The fact that these peptides are more potent against the Cav3.1 current than the Cav1.2 current suggests that the $\alpha_{1.2}$ subunit does not contain transmembrane segments that interact as strongly with the GxxxA motif surrounded by aliphatic residues. This may explain why $\gamma_6$ may preferentially regulate LVA, but not HVA, calcium current in cardiomyocytes.

It has been shown that several tarantula toxins inhibit voltage-gated potassium channels by directly binding to the voltage-sensors of the channels (Lee and MacKinnon, 2004; Milescu et al., 2007). These hydrophobic peptide toxins take advantage of the free energy by partitioning into the lipid bilayer and the location of the target in the protein-lipid interface. Our results suggest that the $\gamma_6$ subunit may function as an endogenous inhibitor of voltage-dependent calcium channels, in part as evidenced by the activity of $\gamma_6$ TM1a as a hydrophobic peptide.

Arikkath and colleagues reported that $\gamma_1$ regulates the Cav1.1, an HVA, current through the first half of the molecule, including TM1 and TM2 (Arikkath et al., 2003). Since both TM1 and TM2 of $\gamma_1$ lack any GxxxA motif with similar sequence context to that of $\gamma_6$ TM1a, it suggests that $\gamma_1$ does not modulate the Cav1.1 current through a mechanism involving interhelical GxxxA motifs that we discussed here. Despite the close similarity in primary sequences between $\gamma_1$ and $\gamma_6$, our data likely describe the evolutionary divergence of these two γ subunits in terms of their mechanisms of modulating voltage-dependent calcium channels.

The observed kinetics may imply a unique mechanism of modulation. We previously showed that $\gamma_6$ inhibits the Cav3.1 current without noticeable changes in the voltage-dependence of activation, inactivation, and kinetics of current deactivation and inactivation (Hansen et al., 2004). This modulatory effect is very unique as compared to modulation of calcium currents by β, $\alpha_2$δ or other γ subunits (see review by Black, 2003; Chen et al., 2007; Dolphin, 2003; Klugbauer et al., 2003). We understand that, with a critical GxxxA motif in TM1, 76 can trap the Cav3.1 channels in a less available state without changing the overall voltage-dependent open probability or single channel conductance. The present disclosure demonstrates that the γ6 TM1a peptide, which contains the GxxxA motif, can directly block the Cav3.1 current by binding with the $\alpha_{3.1}$ subunit (FIGS. 1C and 1D). The current inhibition by $\gamma_6$ TM1a does not cause any changes in voltage dependence of activation or inactivation. Furthermore, the potency of the peptide is not dependent on holding potentials (FIG. 1E), suggesting that $\gamma_6$ TM1a does not preferentially bind to close, open or inactivated channels.

To explain an understanding of the function of $\gamma_6$, we propose a gating scheme for calcium channels in the presence of $\gamma_6$ or $\gamma_6$ TM1a peptide. See Scheme I as illustrated in FIG. 1F. In Scheme I, C, O, and I respectively represent the closed, open, inactivated channels, and B represents the blocker ($\gamma_6$ or $\gamma_6$ TM1a). In the presence of $\gamma_6$, a certain fraction of channels will be blocked and non-conducting, resulting in reduced macroscopic currents. Since $\gamma_6$ does not interfere with voltage-dependent transition steps in the horizontal direction, the activation and inactivation curves should not be affected. However, when analyzed at a single channel level, $\gamma_6$-bound channels are unavailable to open. This scheme suggests that the binding between $\alpha_{3.1}$ and the GxxxA motif of $\gamma_6$ can be dynamic and reversible and is supported by our finding that $\gamma_6$ TM1a can reversibly bind to and dissociated from the Cav3.1 channel. The fast time constants ($A_{fast}$) for binding and unbinding are both smaller than 9 s (FIG. 2), implying that >95% of the binding and dissociation processes are completed within 30 s. Within this time scale, it is very possible for single channels to transition between $\gamma_6$-bound and unbound states and result in a lower availability which we have observed from single channel recordings.

The quick kinetics of interaction are consistent with the idea that $\gamma_6$ directly binds to the Cav3.1 channel through the GxxxA motif in TM1 to preventing ionic flows. The fast inhibition and relaxation of the Cav3.1 current are highly unlikely due to internalization and reinsertion of the performing $\alpha_{3.1}$ subunits in the plasma membrane. Such cellular mechanisms require complex signaling cascades and take several minutes to hours to occur. On the other hand, the possibility is not excluded that the activity of $\gamma_6$ may result in slow internalization or degradation of the $\alpha_{3.1}$ subunits. The presence of a small and much slower component (τ>30 s) in both the binding and unbinding processes, and the existence of an irreversible fraction during current relaxation (FIG. 1D) suggest that $\gamma_6$-bound channels can undergo slower processes which eventually remove the channels from the membrane.

FIG. 1. $\gamma_6$ TM1a peptide inhibits Cav3.1 calcium current in a dose-dependent fashion. (A) Cav3.1 current-voltage (I-V) relationship from a typical HEK/Cav3.1 cell. The holding potential was −100 mV. (B) A representative cell showing the steady-state current amplitude of Cav3.1 currents in the presence of various peptides. Inward calcium currents were elicited at −30 mV. Increasing the concentration of $\gamma_6$ TM1a produced progressive inhibition, while $\gamma_4$ TM1a or a scrambled (SCR) version of $\gamma_6$ TM1a produced little effect. (C) Time course of Cav3.1 current inhibited by 30 µM $\gamma_6$ TM1a in a representative cell. Peak current amplitudes were measured for 30 s in control solution before applying the $\gamma_6$ TM1a solution (arrows). After the current reached a steady-state level, the solution was changed back to control solution (arrowheads). The $\gamma_6$ TM1a washed out, but current returned only to ~88% of the initial level. Therefore, upon the second exposure to the same concentration, current amplitude started at a lower level. (D) When current amplitudes were normalized to the level immediately before $\gamma_6$ TM1a application (indicated arrows), time courses from both peptide applications were nearly identical and not dependent on previous exposure to other peptides. Also shown are the time courses for $\gamma_4$ TM1a and $\gamma_6$ TM1a SCR applications. (E) Dose- and voltage-dependency of α3.1-γ6 TM1a interaction. Increasing the concentration of $\gamma_6$ TM1a produced a greater extent of inhibition of Cav3.1 current. In contrast, holding voltage did not cause a significant shift to the dose-response curve.

Figure 2:
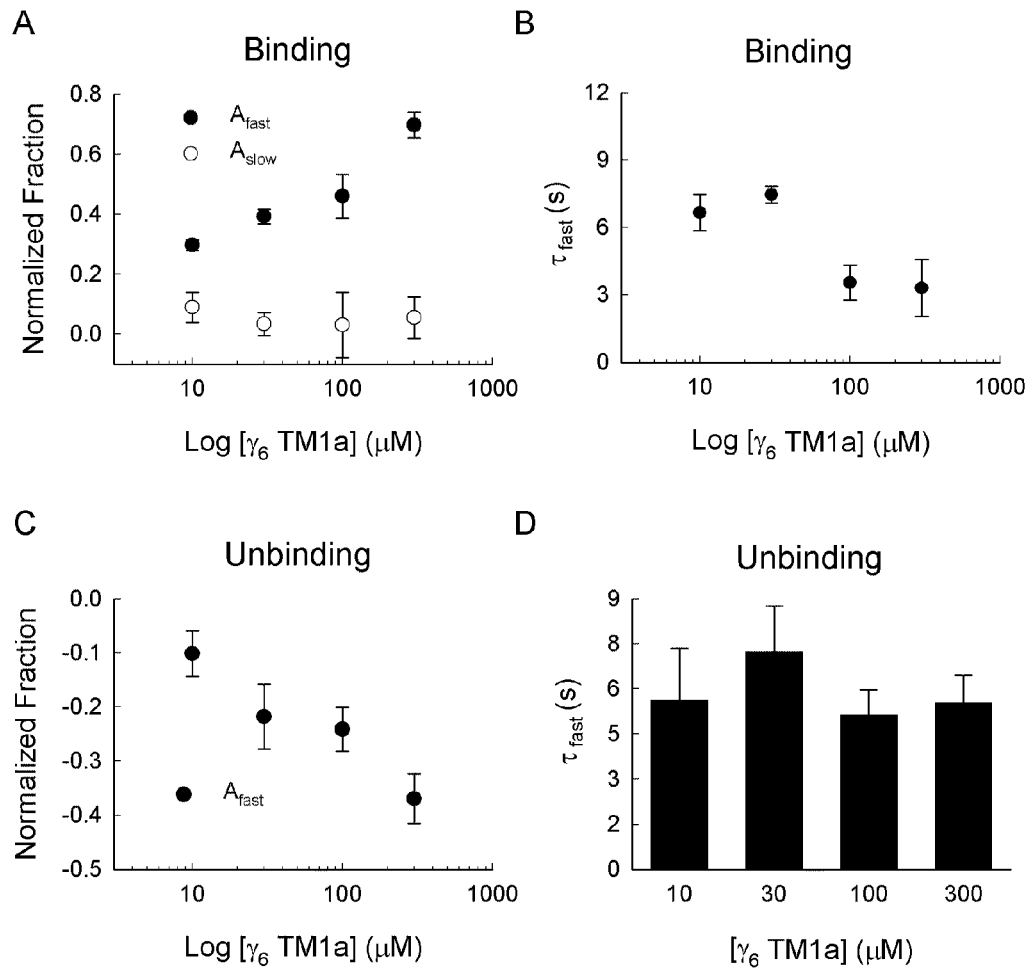
FIG. 2 illustrates kinetics of calcium channel interactions with peptides. (A) Binding data characterized with double exponential fits. (B) Time constants for binding as a function of concentration. (C) Unbinding data. (D) Time constants for unbinding.

FIG. 2. Kinetics of α3.1-$\gamma_6$ TM1a interaction. (A) The binding process was characterized with double exponential fits. The slow component ($A_{slow}$) accounted for less than 10% of the magnitude and was quite variable in fitting. The fast component ($A_{fast}$) accounted for the majority of the current inhibition and displayed a correlation with increased concentration of $\gamma_6$ TM1a peptide. (B) Time constants of the fast component also correlate with concentration of $\gamma_6$ TM1a. As the concentration increased, the time constant decreased. (C) The unbinding process between α3.1 and $\gamma_6$ TM1a was characterized from the recovery of Cav3.1 currents in control solution with double exponential fits. The fast component again dominated the unbinding process and had a good correlation with concentration. (D) The time constants, on the other, were not concentration-dependent.

Figure 3:
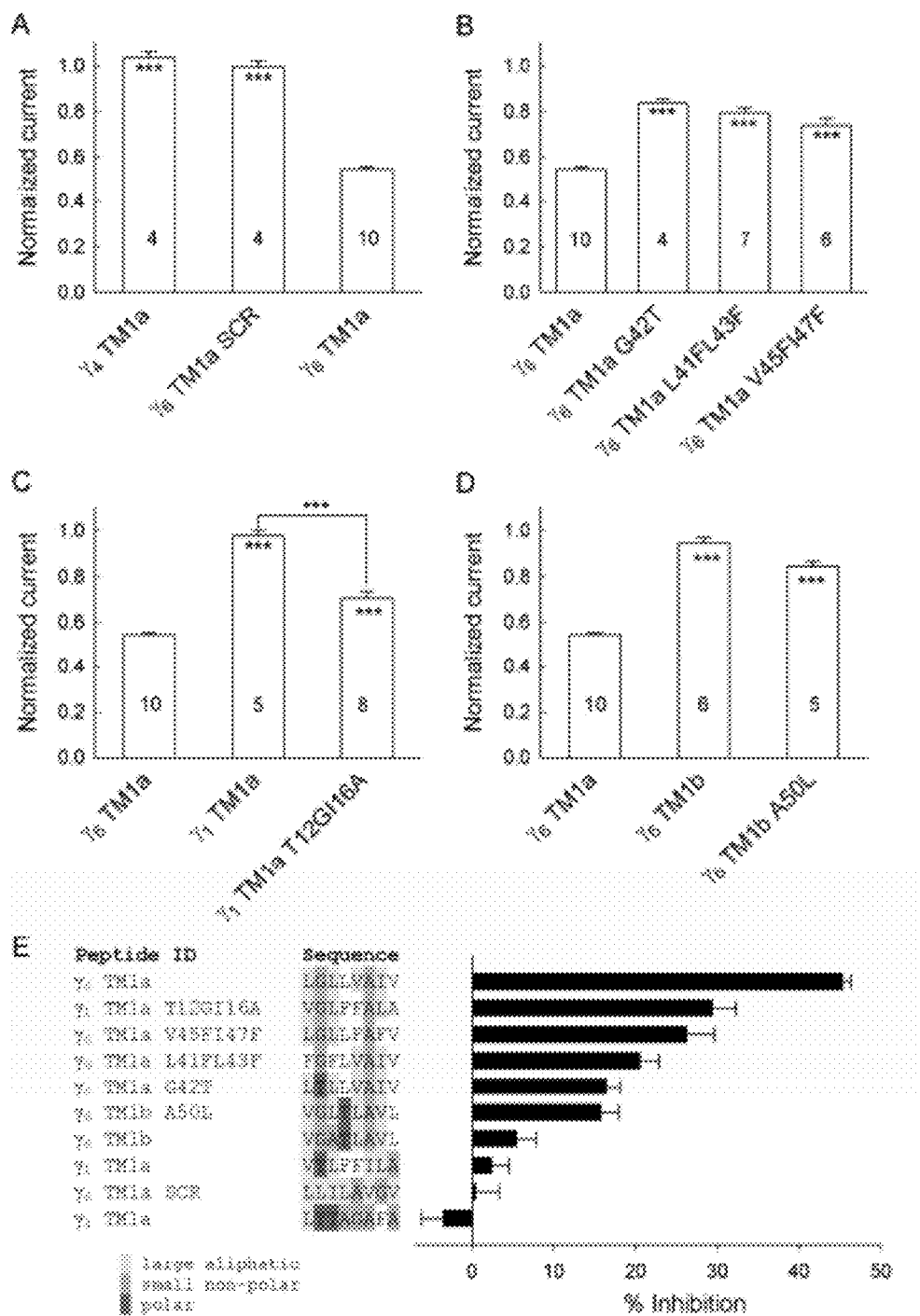
FIG. 3 illustrates the effects of various peptides on LVA calcium channel function (A)-(D). (E) Peptide identity designations and sequences along with percent inhibition of calcium current.

FIG. 3. GxxxA motif and its near neighbor residues determine the efficacies of Cav3.1 current inhibition. All peptides were used at a concentration of 30 µM. Numbers inside bars indicate the number of replicates. Significant differences to $\gamma_6$ TM1a are marked inside the bars, while significant differences between bars are indicated between bars. (A) Summarized effects of three different peptides on Cav3.1 currents. $\gamma_6$ TM1a produced 45.3±1.0% inhibition. In contrast, $\gamma_4$ TM1a and $\gamma_6$ TM1a SCR had no inhibitory effects (−3.5±2.7% and 0.5±2.9%, respectively). (B) Substitution of glycine by threonine in the GxxxA motif (G42T) or replacing its near neighbors (L41 FL43F and V45FI47F) with hydrophobic but non-aliphatic residues reduced the inhibitory effects of the peptides. (C) $\gamma_1$ TM1a does not contain a GxxxA motif and had no inhibitory effect (2.38±2.2%) as compared to $\gamma_6$ TM1a. Creating a GxxxA motif inside $\gamma_1$ TM1a (T12GI16A) which normally does not inhibit current confers the inhibitory effect (29.4±2.9%). (D) $\gamma_6$ TM1b and $\gamma_6$ TM1b A50L have a polar residue in a strongly hydrophobic context. Both of the peptides produced significantly less inhibition than $\gamma_6$ TM1a (p<0.001). (E) Sequences and annotation of the peptides tested. When these peptides are ranked by their relative inhibitory effects on Cav3.1 current, it indicates the importance of a GxxxA motif with near neighbors being large aliphatic residues (I, V, L).

Figure 4:
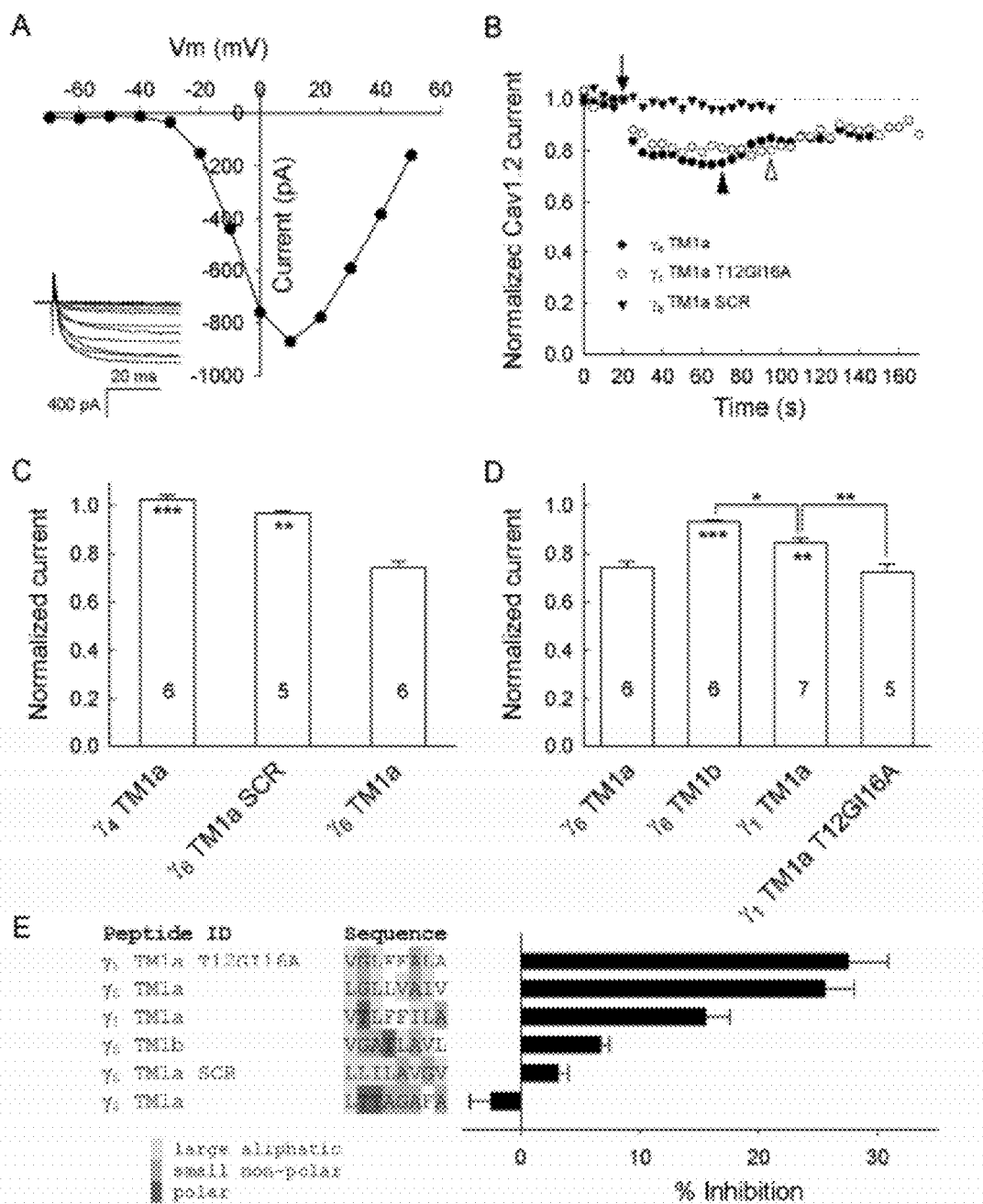
FIG. 4 illustrates the effects of various peptides on HVA calcium channel function (A)-(D). (E) Peptide identity designations and sequences along with percent inhibition of calcium current.

FIG. 4. Small peptides containing the GxxxA motif can also inhibit an HVA (high voltage activated) calcium current (Cav1.2). In some cases HVA inhibition can occur with reduced efficacy relative to LVA inhibition. All peptides were used at a concentration of 30 µM. Numbers inside bars indicate number of replicates. Significant differences to $\gamma_6$ TM1a are marked inside the bars, while significant differences between bars are indicated between bars. (A) Cav1.2 current-voltage (I-V) relationship from a HEK/Cav1.2 cell. Inset: A representative cell expressing inducible Cav1.2 currents 48 hr after induction. Barium currents were elicited at −70 to 50 mV for 60 ms from a holding potential of −100 mV. (B) Representative time courses of Cav1.2 current inhibited by 30 µM $\gamma_6$ TM1a or $\gamma_1$ TM1a T12GI16A. Peak current amplitudes were measured at 0 mV for 25 s in control solution before applying the peptide solutions (arrows). After the current reached a steady-state level, the solutions were changed back to control solution (arrowheads). The inhibitory effects of the peptides washed out incompletely. The $\gamma_6$ TM1a SCR peptide had no inhibitory effect. (C) 74 TM1a and $\gamma_6$ TM1a SCR produced little inhibition (−2.49±1.8% and 3.16±1.8%, respectively) on Cav1.2 current, statistically different from $\gamma_6$ TM1a (25.6±2.4%). (D) Similar to the results on Cav3.1 current, $\gamma_6$ TM1b and $\gamma_1$ TM1a (6.72±1.8% and 15.5±5.3%, respectively) demonstrated activity but produced much less inhibition as compared to $\gamma_6$ TM1a. In contrast, $\gamma_1$ TM1a T12GI16A is active and as effective as $\gamma_6$ TM1a (27.5±3.3%; p>0.05) on Cav1.2 current. (E) When peptides that were tested on Cav1.2 current are ranked by their relative efficacies, it also indicated the importance of a GxxxA motif surrounded by aliphatic residues.

REFERENCES INCLUDING SUCH FOR EXAMPLE 1

Arikkath J and Campbell K P (2003) Auxiliary subunits: essential components of the voltage-gated calcium channel complex. Curr Opin Neurobiol 13:298-307.

Arikkath J, Chen C C, Ahern C, Allamand V, Flanagan J D, Coronado R, Gregg R G and Campbell K P (2003) Gamma 1 subunit interactions within the skeletal muscle L-type voltage-gated calcium channels. J Biol Chem 278:1212-9.

Black J L, 3rd (2003) The voltage-gated calcium channel gamma subunits: a review of the literature. J Bioenerg Biomembr 35:649-60.

Burgess D L, Gefrides L A, Foreman P J and Noebels J L (2001) A Cluster of Three Novel Ca(2+) Channel gamma Subunit Genes on Chromosome 19q13.4: Evolution and Expression Profile of the gamma Subunit Gene Family. Genomics 71:339-350.

Chen L, Chetkovich D M, Petralia R S, Sweeney N T, Kawasaki Y, Wenthold R J, Bredt D S and Nicoll R A (2000) Stargazin regulates synaptic targeting of AMPA receptors by two distinct mechanisms. Nature 408:936-43.

Chen R-S, Deng T-C, Garcia T, Sellers Z M and Best P M (2007) Calcium channel gamma subunits: a functionally diverse protein family. Cell Biochem Biophys 47:178-186.

Chu P J, Robertson H M and Best P M (2001) Calcium channel gamma subunits provide insights into the evolution of this gene family. Gene 280:37-48.

Curran A R and Engelman D M (2003) Sequence motifs, polar interactions and conformational changes in helical membrane proteins. Curr Opin Struct Biol 13:412-7.

Dolphin A C (2003) Beta subunits of voltage-gated calcium channels. J Bioenerg Biomembr 35:599-620.

Ertel E A, Campbell K P, Harpold M M, Hofmann F, Mori Y, Perez-Reyes E, Schwartz A, Snutch T P, Tanabe T, Birnbaumer L, Tsien R W and Catterall W A (2000) Nomenclature of voltage-gated calcium channels. Neuron 25:533-5.

Freise D, Held B, Wissenbach U, Pfeifer A, Trost C, Himmerkus N, Schweig U, Freichel M, Biel M, Hofmann F, Hoth M and Flockerzi V (2000) Absence of the gamma subunit of the skeletal muscle dihydropyridine receptor increases L-type Ca2+ currents and alters channel inactivation properties. J Biol Chem 275:14476-81.

Hansen J P, Chen R S, Larsen J K, Chu P J, Janes D M, Weis K E and Best P M (2004) Calcium channel gamma6 subunits are unique modulators of low voltage-activated (Cav3.1) calcium current. J Mol Cell Cardiol 37:1147-58.

Held B, Freise D, Freichel M, Hoth M and Flockerzi V (2002) Skeletal muscle L-type Ca(2+) current modulation in gamma1-deficient and wildtype murine myotubes by the gamma1 subunit and cAMP. J Physiol 539:459-68.

Huang B, Qin D, Deng L, Boutjdir M and N E-S (2000) Reexpression of T-type Ca2+ channel gene and current in post-infarction remodeled rat left ventricle. Cardiovasc Res 46:442-9.

Jay S D, Ellis S B, McCue A F, Williams M E, Vedvick T S, Harpold M M and Campbell K P (1990) Primary structure of the gamma subunit of the DHP-sensitive calcium channel from skeletal muscle. Science 248:490-2.

Kleiger G and Eisenberg D (2002) GXXXG and GXXXA motifs stabilize FAD and NAD(P)-binding Rossmann folds through C(alpha)-H . . . O hydrogen bonds and van der waals interactions. J Mol Biol 323:69-76.

Klugbauer N, Marais E and Hofmann F (2003) Calcium channel alpha2delta subunits: differential expression, function, and drug binding. J Bioenerg Biomembr 35:639-47.

Larsen J K, Mitchell J W and Best P M (2002) Quantitative analysis of the expression and distribution of calcium channel alpha 1 subunit mRNA in the atria and ventricles of the rat heart. J Mol Cell Cardiol 34:519-32.

Lee S Y and MacKinnon R (2004) A membrane-access mechanism of ion channel inhibition by voltage sensor toxins from spider venom. Nature 430:232-5.

McCleskey E W (1994) Calcium channels: cellular roles and molecular mechanisms. Curr Opin Neurobiol 4:304-12.

Milescu M, Vobecky J, Roh S H, Kim S H, Jung H J, Kim J I and Swartz K J (2007) Tarantula toxins interact with voltage sensors within lipid membranes. J Gen Physiol 130:497-511.

Moss F J, Viard P, Davies A, Bertaso F, Page K M, Graham A, Canti C, Plumpton M, Plumpton C, Clare J J and Dolphin A C (2002) The novel product of a five-exon stargazin-related gene abolishes Ca(V)2.2 calcium channel expression. Embo J 21:1514-23.

Neely A, Wei X, Olcese R, Birnbaumer L and Stefani E (1993) Potentiation by the beta subunit of the ratio of the ionic current to the charge movement in the cardiac calcium channel. Science 262:575-8.

Russ W P and Engelman D M (2000) The GxxxG motif: a framework for transmembrane helix-helix association. J Mol Biol 296:911-9.

Schneider D and Engelman D M (2004) Motifs of two small residues can assist but are not sufficient to mediate transmembrane helix interactions. J Mol Biol 343:799-804.

Senes A, Engel D E and DeGrado W F (2004) Folding of helical membrane proteins: the role of polar, GxxxG-like and proline motifs. Curr Opin Struct Biol 14:465-79.

Senes A, Gerstein M and Engelman D M (2000) Statistical analysis of amino acid patterns in transmembrane helices: the GxxxG motif occurs frequently and in association with beta-branched residues at neighboring positions. J Mol Biol 296:921-36.

Takebayashi S, Li Y, Kaku T, Inagaki S, Hashimoto Y, Kimura K, Miyamoto S, Hadama T and Ono K (2006) Remodeling excitation-contraction coupling of hypertrophied ventricular myocytes is dependent on T-type calcium channels expression. Biochem Biophys Res Commun 345:766-73.

Tomita S, Chen L, Kawasaki Y, Petralia R S, Wenthold R J, Nicoll R A and Bredt D S (2003) Functional studies and distribution define a family of transmembrane AMPA receptor regulatory proteins. J Cell Biol 161:805-16.

Vassort G, Talayera K and Alvarez J L (2006) Role of T-type Ca2+ channels in the heart. Cell Calcium 40:205-20.

Supplement to Example 1.

Further experiments and analysis of experiments described above were performed. See, for example, results indicated in FIG. 5, FIG. 6, and Table 3.

TABLE 3

Effect of Gamma6 TM1a peptide on Cav3.1 inactivation and activation curves.

| Item | Control | 30 uM | 100 uM | 300 uM | Wash[a] |
|---|---|---|---|---|---|
| Inactivation | | | | | |
| $V_h$ (mV) | −74.4 ± 1.1 (n = 8) | −76.6 ± 2.4 (n = 5) | −80.4 ± 4.2 (n = 2) | −80.3 ± 1.8 (n = 4)[b] | 76.4 ± 2.4 (n = 2) |
| k | 9.0 ± 0.4 (n = 8) | 10.1 ± 0.3 (n = 5) | 9.7 ± 1.0 (n = 2) | 10.7 ± 0.6 (n = 4) | 7.4 ± 0.8 (n = 2) |
| Activation | | | | | |
| $V_h$ (mV) | −48.3 ± 3.8 (n = 3) | | | −47.6 ± 3.6 (n = 3) | |
| k | −6.1 ± 1.1 (n = 3) | | | −6.9 ± 1.3 (n = 3) | |

[a]After washout from 300 uM.
[b]Significantly different from the control group when one-tailed paired t-test is used (p = 0.0278).

The data for "Wash" are for conditions after washout from 300 μM. Upon review of these results, no significant differences are found in the activation or inactivation parameters in all groups when compared with the controls.

Results

In this study we tested many peptides, the names and sequences of which are listed in FIG. 5A. We determined the structure of peptides such as the γ6 TM1a peptide in connection with the ability to inhibit calcium current. We demonstrated such inhibition including for Cav3.1 current. The γ6 TM1a peptide (the first half of γ6 TM1) contains residues 41 through 48 of the native γ6 protein with the critical GxxxA motif at its center. The Cav3.1 calcium current-voltage relationship (FIG. 5B) peaked at either −40 or −30 mV, and −30 mV was used in subsequent experiments to evaluate the efficacy of the peptides on the Cav3.1 current. The γ6 TM1a peptide applied in the extracellular solution inhibited the Cav3.1 calcium current in a dose-dependent manner (FIGS. 5B,C). The peptide does not appear to change the shape or the reversal potential of the I-V plot. However, the inhibition is not completely reversible (FIGS. 5B,C). When the calcium currents are normalized and displayed at expanded time scale, it becomes obvious to us that the γ6 TM1a does not modify the current inactivation process.

Some sodium and calcium channel blockers such as phenyloin and mibefradil selectively inhibit inactivated channels and therefore exhibit state- or voltage-dependent block (Kuo and Bean, 1994; Martin et al., 2000). In this scenario, the drugs produce little block at hyperpolarized holding potentials when channels are largely in resting state. Increasing channel inactivation by depolarizing the membrane dramatically increases the drug affinity. To test whether γ6 TM1a inhibits Cav3.1 current in a voltage-dependent manner, the extent of steady-state current inhibition by γ6 TM1a was measured under −130, −100 or −80 mV holding potentials. As shown in FIG. 5D, the apparent affinity ($K_{app}$) for γ6 TM1a at −130 mV is 105 μM. At −100 and −80 mV, the $K_{app}$ decreases to 42 and 35 μM, respectively. This indicates a mere 3-fold increase in drug affinity over a 50 mV change in holding potential (and ~50% reduction in channel availability, see FIG. 5E). The extent of current inhibition does not vary much between −130 mV (~100% channel availability) and −80 mV (~55% channel availability) at 10, 30 or 100 μM, arguing against a typical voltage-dependent blocking mechanism. Furthermore, if γ6 TM1a preferentially inhibits inactivated Cav3.1 channel, the presence of peptide may stabilize inactivated channel and thus cause a significant left shift of the inactivation curve. When Cav3.1 inactivation curves were assayed in 30 μM γ6 TM1a, no obvious shift was detected. Only when 100 and 300 μM peptides were tested, the shifts became observable (FIG. 5E). However, since intrinsic variability in the half inactivation voltage (Vh) exists as we have observed (Hansen et al., 2004; Lin et al., 2008), we did not find statistically meaningful shift unless we used one-tailed paired t-test for 300 μM peptide (ΔVh=−5.9 mV). Even if we consider the shift of inactivation curve significant, the reduction in channel availability (e.g. <5% at −100 mV and 100 μM, FIG. 5E) is far less than adequate to account for the extent of current inhibition (~60% at −100 mV and 100 μM, FIG. 5D). We also noticed that after the 300 μM peptide treatment, the inactivation curve does not completely reverse back to its control curve even after the current has reached steady state in wash solution. This should not cause a major concern when we only use peptides at 30 μM as further shown herein. We next examined the voltage-dependent activation of Cav3.1 current in the γ6 TM1a peptide. As shown in FIG. 1F, Cav3.1 current activation is virtually identical in control or the peptide solutions. Taken together, these results illustrate that γ6 TM1a does not change the I-V curve, inactivation kinetics, activation curve; only has a minor effect on the inactivation curve; and increases affinity slightly as channel availability is reduced. Therefore, the reduction (~60%) of Cav3.1 current by 100 μM peptide at −100 mV (availability ~90%, FIG. 5E) is mostly due to the inhibition of both resting and inactivated channels. The parameters of voltage-dependent inactivation and activation of the Cav3.1 current with and without the presence of the γ6 TM1a peptide are summarized in Table 3.

While assaying the effect of the peptide on the Cav3.1 current, we noticed that the inhibition occurs over a time course of several seconds to a few minutes. The recovery of current in washout is also a slow process. In FIG. 1C (see also previous discussion in Example 1 for this data), the calcium current recovered from ~55% to ~88% of its control level, indicating that most of the inhibition was reversible. However, in all of the cells tested with γ6 TM1a, a small portion of the current never recovered suggesting that γ6 TM1a-α3.1 interaction features both reversible and irreversible fractions. We also found that the irreversible portion does not affect the inhibition process upon the next exposure to the same solution. When calcium currents are normalized to the control current amplitude immediately before switching into the peptide solution, both exposures result in nearly identical time courses (FIG. 1D; (see also previous discussion in Example 1 for this data)). This allowed us to test multiple peptides at various dosages on a single cell without worrying about confounding effect from previous peptide exposure. Using the same cell, we also demonstrated that control peptides from γ4 TM1 (γ4 TM1a) or a scrambled version of γ6 TM1a (γ6 TM1a SCR) had no effect on the Cav3.1 current.

Analysis of the kinetics of the Cav3.1 current inhibition further illustrates the dose-dependent nature of the of γ6 TM1a-α3.1 interaction, as would be expected from conventional drug-receptor interactions. When the inhibition process is characterized by fitting the time course with a biexponential curve, the dominant component (Afast) displays a strong correlation with the concentration of γ6 TM1a (FIG. 6A) and accounts for the extent of current inhibition shown in FIG. 1D. On the other hand, the minor component ($A_{slow}$) accounts for less than 12% of the current amplitude and has no apparent correlation with the peptide concentration. When the time constant of the dominant component (τfast) is plotted against γ6 TM1a concentration, a general trend exists in which the time constant decreases when the peptide concentration increases (FIG. 6B). The recovery process, fitted with bi-exponential components from the relaxation of Cav3.1 current upon removing the γ6 TM1a peptide (as in FIG. 1D), also revealed the drug-like nature of γ6 TM1a. The dominant (and fast) component of the recovery process was positively correlated with concentration. The extent of Cav3.1 current fast recovery was greatest following exposure to 300 μM ($A_{fast}$=0.37±0.05, FIG. 6C), a concentration in which the Cav3.1 inhibition was largest (79.3±7.5%, FIG. 6A). The time constant of the dissociation process is not concentration dependent (FIG. 6D) and offers an estimate of the dissociation rate (β=⅙ s, or 0.167 s−1).

GxxxA motif and surrounding residues determine efficacy of Cav3.1 current inhibition. FIG. 3A shows the summarized effects of three peptides on the Cav3.1 current at 30 μM. In contrast to γ6 TM1a, which inhibits the Cav3.1 current by 45.3±1.0%, γ4 TM1a and γ6 TM1a SCR cause no inhibitory effects (−3.5±2.7% and 0.5±2.9%, respectively). This result indicates that the inhibition of the Cav3.1 current by γ6 TM1a requires a specific sequence context. To further explore the sequence context that mediates the γ6 TM1a-α3.1 interaction, we tested 8-AA peptides containing mutated residues of γ6 TM1a and sequences from γ6 TM1b and γ1 TM1a. Because many of the peptides we reported here are relatively hydrophobic, it was sometimes impossible to obtain concentrations above 30 μM in the control solution. Consequently, we generally proceeded to apply all peptides at 30 μM. We first disrupted the GxxxA motif by substituting the glycine at position 42 of the γ6 TM1a with leucine, an aliphatic residue. The mutant peptide (γ6 TM1a G42L: LLLLVAIV) was so hydrophobic that it failed to be synthesized. We then tried to substitute the glycine with threonine, a polar residue. The substitution (γ6 TM1a G42T) greatly enhances the solubility of the peptide. 30 μM of γ6 TM1a G42T and was active, however, only inhibits the Cav3.1 current by 16.4±1.7%, significantly less than the wildtype γ6 TM1a (p<0.001). We next replaced the aliphatic residues at the adjoining positions of the GxxxA motif with phenylalanine, a hydrophobic but non-aliphatic residue. These substitutions also demonstrate activity but relatively reduce the potencies of the peptides (γ6

TM1a L41 FL43F: 20.6±2.2%; γ6 TM1a V45FI47F: 26.3±3.3%). Taken together, these results indicate that both the GxxxA framework and its neighboring aliphatic residues are involved in the γ6 TM1a-α3.1 interaction.

Our work using full-length γ proteins indicates that γ1, which lacks a GxxxA motif in the first half of TM1, does not inhibit Cav3.1 current (Lin et al., 2008). This result suggests that γ1 TM1a, if used in a peptide form, should also produce little inhibitory effect on the Cav3.1 current and we have observed that γ1 TM1a had little effect on Cav3.1 calcium current (current inhibition=2.4±2.2%, FIG. 3C). However, when we introduced a GxxxA motif into the γ1 peptide (γ1 TM1a T12GI16A) it became a significantly active inhibitor (29.4±2.9%, FIG. 3C). This result is consistent with our previous results obtained from the use of full-length γ proteins and confirms the importance of the GxxxA motif (Lin et al., 2008).

The second half of γ6 TM1 also contains a G49xxxA53 motif, but it is not implicated in the inhibition of the Cav3.1 current by γ6 (Lin et al., 2008). When the peptide γ6 TM1b (containing residues 48 through 55 of wild-type γ6) was tested, it produced a very small (5.5±2.3%) inhibition on Cav3.1 current. Careful examination of the sequences of γ6 TM1a and γ6 TM1b reveals that γ6 TM1b has an Ala50 in the adjoining position of Gly49, and Thr51 in the center of the GxxxA motif. Substituting the alanine with leucine (γ6 TM1b A50L) only slightly increased the extent of current inhibition (15.8±2.2%). Despite having a complete GxxxA motif surrounded by aliphatic residues, TM1b A50L is less potent than γ6 TM1a as a Cav3.1 current inhibitor, suggesting that the hydroxyl group from Thr51 could be disruptive of the γ6-α3.1 interaction.

With the tested peptides ranked by their potency of inhibiting the Cav3.1 current at 30 μM, we demonstrate that peptides without a complete GxxxA motif (γ6 TM1a SCR and γ1 TM1a) are unable to reduce the Cav3.1 current; that a polar threonine residue in the center of a GxxxA motif (γ6 TM1b, γ6 TM1b A50L) can disrupt the interaction; and that hydrophobic interactions provided by aliphatic residues around the GxxxA framework (γ6 TM1a, γ1 TM1a T12GI16A) provide useful and possibly the optimal interaction between the γ6 TM1a peptide and the Cav3.1 channel.

γ6 TM1a peptide inhibits Cav1.2 current with reduced efficacy. Our studies have demonstrated that γ6 selectively reduces LVA, but not HVA, calcium current when overexpressed by adenovirus in rat atrial myocytes (Lin et al., 2008). This suggests that γ6 TM1a, when tested in a peptide form, should produce relatively weak, if any, inhibition of the Cav1.2 current. To test this hypothesis, we performed a similar series of recordings on HEK 293 cells expressing tetracycline-inducible Cav1.2 currents.

Cells expressing Cav1.2 produce the long-lasting, non-inactivating barium currents typical of this HVA channel (FIG. 4A). Exposure of the cells to the peptide γ6 TM1a cause a modest inhibition of current (25.6±2.4%, FIGS. 4B, C) that is not seen with the control peptides γ6 TM1a SCR or γ4 TM1a (−2.5±1.8% and 3.2±0.8%, respectively) (FIGS. 4B, C). The γ6 TM1b is even less effective as an inhibitor of Cav1.2 current (6.7±0.7%, FIG. 4D). γ1 TM1a, although significantly less potent than γ6 TM1a, inhibits the Cav1.2 current by 15.5±2.0% (FIG. 4D). Introducing a GxxxA motif into γ1 TM1a further enhances the current inhibition by γ1 TM1a T12GI16A to 27.5±3.3%, making it as potent as γ6 TM1a in inhibiting the Cav1.2 current (FIG. 4D). When the various peptides were ranked by their efficacies in reducing Cav1.2 current (FIG. 4E), it is apparent that a GxxxA framework and hydrophobic interactions are important elements for inhibition. Taken together, our results from the Cav1.2 current recordings indicate that γ6 TM1a is capable of suppressing the Cav1.2 current through the GxxxA motif and its surrounding hydrophobic residues. However, the extent of current inhibition produced by γ6 TM1a is greater on the Cav3.1 than on the Cav1.2 current (cf. FIGS. 3E & 4E).

Figure 5:
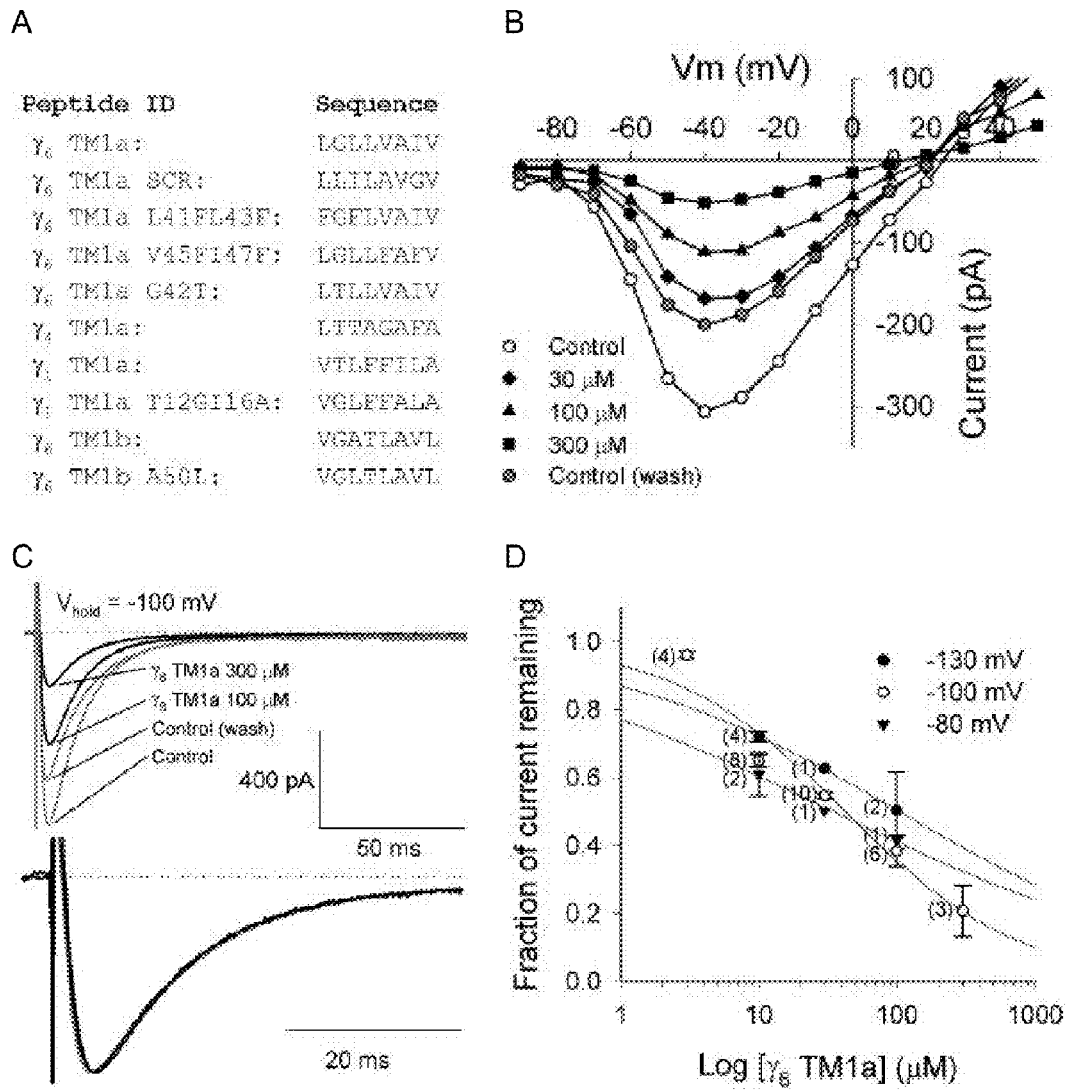
FIG. 5 illustrates results of studies with various peptides including the demonstration of the inhibition of calcium current.
Figure 5:
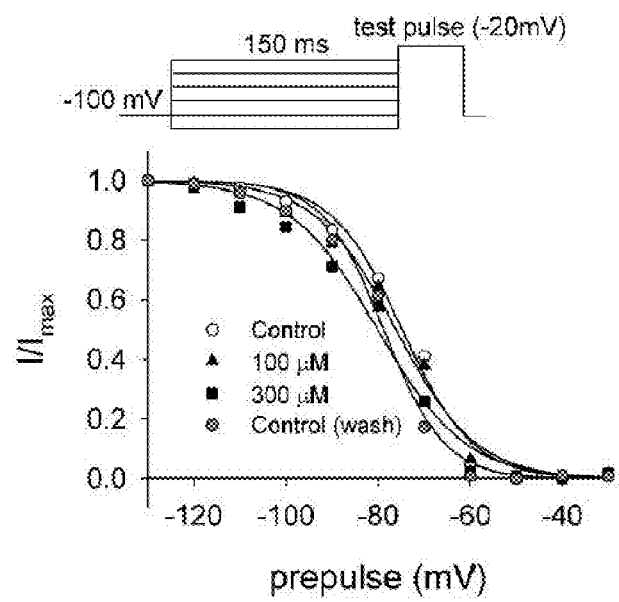
Figure 5:
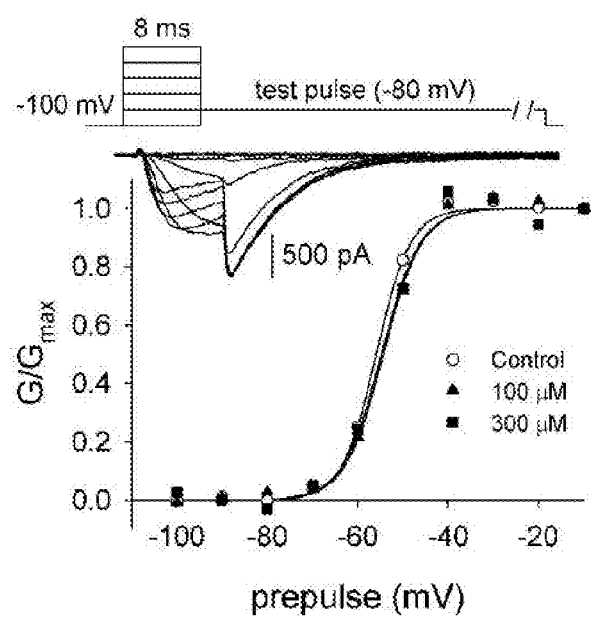
Figure 6:
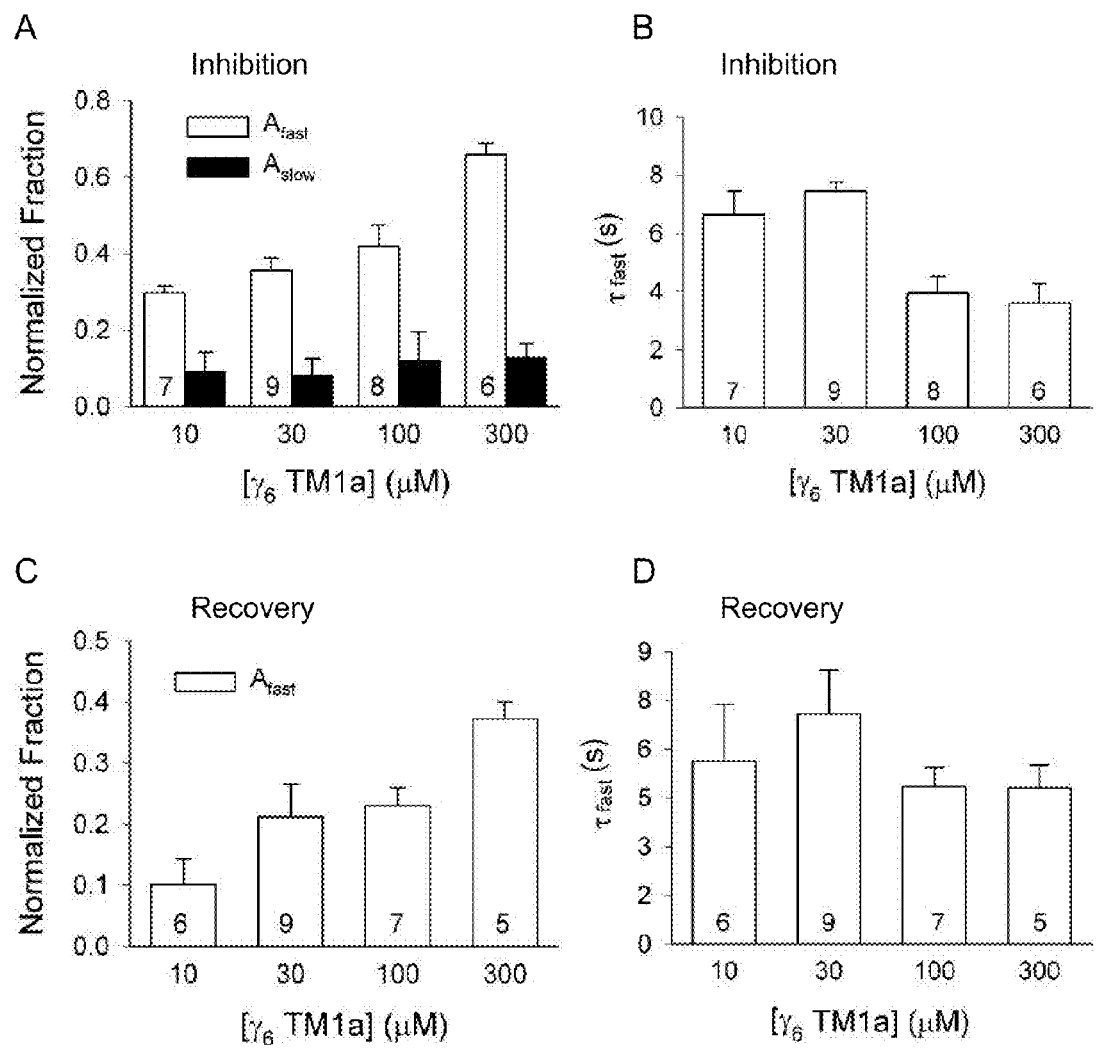
FIG. 6 illustrates results of studies with various peptides including the demonstration of kinetics of interactions between peptides and calcium channels.

Summary of Information Regarding FIG. 5 and FIG. 6

FIG. 5. γ6 TM1a peptide inhibits Cav3.1 calcium current in a dose-dependent fashion. (A) List of sequences of the peptides that were used in this study. (B) Cav3.1 current-voltage (I-V) relationship from a typical HEK/Cav3.1 cell. The holding potential was −100 mV. (C) Top: a representative cell showing the steady-state current amplitude of Cav3.1 currents in the presence of γ6 TM1a peptides. Inward calcium currents were elicited at −30 mV. Increasing the concentration of γ6 TM1a produced progressive inhibition. Bottom: normalized current traces displayed at expanded time scale. (D) Dose- and voltage-dependency of α3.1-γ6 TM1a interaction. Numbers by the symbols represent number of replicates. Gray lines are Hill equation fits to the data with the form $1/[1+(\text{concentration}/K_{app})n]$. The $K_{app}$ values are 105, 42, 35 μM and n values are 0.41, 0.69, 0.34 at −130, −100, −80 mV, respectively. (E) Cav3.1 inactivation curves assayed from a representative cell by a conventional two-pulse protocol are fitted with the Boltzmann function (solid lines). Half inactivation voltages in control, 100 μM, 300 μM and wash are −74.8, −76.2, −80.1 and −78.8 mV, respectively. (F) Cav3.1 activation curves measured from a representative cell by tail currents at −80 mV with online p/−4 leak subtraction are fitted with the Boltzmann function (solid lines). Half activation voltages in control, 100 μM and 300 μM solutions are −55.9, −54.4 and −54.8 mV. The inset shows the representative tail currents obtained in control solution after current activation for 8 ms at −100 to −10 mV.

For FIG. 5B see also FIG. 1A. For FIG. 5D see also FIG. 1E.

FIG. 6. Kinetics of α3.1-γ6 TM1a interaction. [See also FIG. 2A, Time course of Cav3.1 current inhibited by 30 μM γ6 TM1a in a representative cell. Peak current amplitudes were measured for 30 s in control solution before applying the γ6 TM1a solution (arrows). After the current reached the steady-state level, the solution was changed back to control solution (arrowheads). The γ6 TM1a clearly washed out, but the current only returned to ~88% of the initial level. Therefore, upon the second exposure to the same concentration, current amplitude started at a lower level. FIG. 2B: When current amplitudes were normalized to the level immediately before γ6 TM1a application (indicated arrows), time courses from both peptide applications were nearly identical and not influenced by previous exposure to other peptides. Also shown are the time courses for γ4 TM1a and γ6 TM1a SCR applications.] FIG. 6(A) The inhibition process was characterized with double exponential fits. Normalized fraction is the fitted amplitude of the exponential component when control current is normalized to 1. The slow component ($A_{slow}$) accounted for less than 12% of the magnitude and was quite variable in fitting. The fast component ($A_{fast}$) accounted for the majority of the current inhibition and displayed a nice correlation with increased concentration of γ6 TM1a peptide. FIG. 6(B) Time constants of the fast component generally decrease with the increase of γ6 TM1a concentration. FIG. 6(C) The recovery of Cav3.1 current in control solution was characterized with double exponential fits. The fast component dominated the recovery process and had a good correlation with concentration. FIG. 6(D) The time constants were not concentration-dependent.

In considering underlying explanations for the observed activities, we determined that the kinetics are consistent with a unique mechanism of modulation. We previously showed that γ6 inhibits the Cav3.1 current without noticeable changes in the voltage-dependence of activation, inactivation, and kinetics of current deactivation and inactivation (Hansen et al., 2004). In contrast to modulation of calcium currents by β, α2δ or other γ subunits that changes the surface expression of the channel or voltage-dependence of activation and/or inactivation, this modulatory effect is rather unique. With a critical GxxxA motif in TM1, γ6 can trap the Cav3.1 channels in a less available state without changing the overall voltage-dependent open probability or single channel conductance (Lin et al., 2008). Our results further demonstrate that the γ6 TM1a peptide, which contains the GxxxA motif, can directly inhibit the Cav3.1 current. Importantly in contrast to many gating modifiers, the current inhibition by γ6 TM1a does not cause significant changes in voltage-dependence of activation or inactivation. Furthermore, holding potential does not drastically alter the potency of the peptide, indicating that γ6 TM1a binds both closed and inactivated channels relatively independent of membrane potential. Our analysis also found that the Hill coefficient of the γ6 TM1a/α3.1 interaction to be less than 1, indicating a negative cooperativity. Because the exact stoichiometry of the calcium channel with subunits are unknown, we do not know how many binding sites exist on a α subunit for the γ subunit. A negative cooperativity therefore may indicate a competition between individual peptides for a single binding site.

Several tarantula toxins were found to inhibit voltage-gated potassium channels by directly binding to the voltage sensors of the channels (Lee and MacKinnon, 2004; Milescu et al., 2007). These hydrophobic peptide toxins partition into the lipid bilayer and interact with the target at the protein-lipid interface. Given that γ6 TM1a is a hydrophobic peptide from a transmembrane helix, we believe that γ6 may function as an endogenous Cav3.1 channel antagonist within the membrane. Although the exact γ6 binding site on α3.1 is still unknown, it may lie in a transmembrane segment situated at the perimeter of the channel. Because γ6 TM1a does not cause a shift in the Cav3.1 activation curve, voltage sensors are likely not the major targets. Moreover, the insensitivity of affinity to voltage indicates that voltage-dependent block is unlikely the major mechanism of action, either. This leaves us with the possibility that γ6 TM1a works as a pore blocker. Meanwhile, the hydrophobicity, the requirement of GxxxA motif, and the consistency of results from targeted mutations in small peptides and whole γ6 proteins all support the idea that the γ6 TM1a peptide works as if it were in its native environment, i.e. within the membrane.

The fast inhibition and relaxation of the Cav3.1 current support the idea that γ6 directly binds to the Cav3.1 channel through the GxxxA motif in TM1. The quick kinetics is unlikely to be mediated by internalization and reinsertion of the pore-forming α3.1 subunits in the plasma membrane. Such cellular mechanisms require complex signaling cascades and take several minutes or hours to occur. On the other hand, our data do not exclude the possibility that the activity of α6 may result in slow internalization of the α3.1 subunits. In fact, the presence of a small and slower component (τ>30 s) in both the inhibition and recovery processes, and the existence of an irreversible fraction during current relaxation suggest that γ6-bound channels can undergo processes that eventually remove the channels from the membrane. Interestingly, γ6 co-immunoprecipitates with α3.1 in both HEK cells and atrial myocytes (Lin et al., 2008). Given the low affinity ($K_{app}$=~50 μM) and dynamic nature of the interaction between α3.1 and γ6 TM1a, it seems unlikely that the GxxxA motif in γ6 TM1 mediates the strong γ6-α3.1 binding as probed by co-immunoprecipitation. Therefore, the function of the GxxxA motif in γ6 TM1 seems to be dynamically silencing the Cav3.1 channels on the membrane, while another part of γ6 may provide a stronger association with the channel. This strong association may lead to channel internalization and/or degradation.

It is noted that an effect of an embodiment of the invention on LVA current in native cardiac myocytes establishes the ability to affect a Cav3.2 channel. Therefore in embodiments of compositions and methods, Cav3.2 channels are regulated.

EXAMPLE 2

Therapeutic Applications

Physiological roles and therapeutic applications. The auxiliary subunits β and $α_2δ$ modulate voltage voltage-dependent calcium channels by promoting the membrane insertion of the $α_1$ subunits, and by enhancing channel activities. It has been reported that $γ_6$ is robustly expressed in muscular tissues (Chu et al., 2001). The present disclosure describes that certain $γ_6$ proteins and peptides can display activity and in some cases a preferentially higher affinity towards LVA current. In embodiments, compositions including peptides of the invention can serve to regulate calcium current, for example, the subtle but critical amount of window current through LVA calcium channels in pace-maker cells and atrial myocytes. Compositions of the invention including $γ_6$ based peptides may do so by establishing and/or regulating a dynamic equilibrium with the amount of active LVA channels in the membrane and targeting excessive channels for recycling. Adult ventricular myocytes robustly express $γ_6$, as well as mRNA of the $α_{3.1}$ and $α_{3.2}$ subunits (Larsen et al., 2002), but normally no LVA currents are detectable in these cells. However, the remodeling of hypertrophied or post-infarcted ventricular myocytes is often accompanied by the re-occurrence of LVA current and increase in mRNA levels of the Cav3.1 and Cav3.2 channels (Huang et al., 2000; Takebayashi et al., 2006). Therefore in further embodiments, compositions of the invention are able to provide an early and efficient way of modifying LVA currents. Such embodiments of compositions and methods of administering compositions to cells can result in performance which is considerably faster than regulation which could occur by the biosynthesis of new channels from mRNA or gene transcriptions.

Voltage dependent calcium channels are multimeric proteins that reside in the surface membranes of cells. The activation of these channels is involved in cellular functions such as the release of neurotransmitters, muscle contraction, and the transmission of pain signals. Compositions and methods of the invention include agents capable of altering calcium channel function which therefore can modify cellular and physiological processes.

Compositions herein including peptides can be useful in affecting calcium channel function in mammalian cells. In embodiments, compositions and methods are useful in regulating, particularly inhibiting, calcium in mammalian nerve and muscle cells. In specific embodiments there are methods of inhibiting voltage dependent calcium current. Compositions of the invention are useful in conditions and disorders relating to calcium channel function and in particular for regulation of calcium current. For example, certain peptides of the invention can inhibit LVA currents in cardiomyocytes. In embodiments, compositions of the invention are used as therapeutic agents in treating pathological hyper-excitability, such as cardiac arrhythmia and neural epilepsy.

In an embodiment, the disorder is cardiac hypertrophy. In an embodiment, the disorder is cellular hypertrophy. In an embodiment, an aspect of the invention is useful in the context of a pathological hypertrophy in connection with LVA calcium current, particularly including a Cav3.2 family member. In an embodiment, the disorder is a cardiomyopathy. In embodiments, compositions and methods are useful in the context of an induction of calcineurin/NFAT hypertrophic signaling, pressure overload-induced hypertrophy, and angiotensin II-induced cardiac hypertrophy.

Further embodiments relate to pathophysiological conditions for chronic pain and other aspects of heart disease, including such which are amenable to effects of agents which block calcium channel function. Applications include such in connection with conditions of angina, hypertension, cardiomyopathies, supraventricular arrhythmias, aesophogeal achalasia, premature labor and Raynaud's disease. Embodiments of compositions and methods are also useful in the study of the physiology of cells including, but not limited to, cells of the nervous and muscular system.

In the central nervous system, exogenous γ6 TM1a peptide may be utilized to alleviate Cav3.1 current-related neuronal hyper-excitability, such as absence seizure or temporal lobe epilepsy. This can extend to include situations where γ6 is not normally expressed.

Compositions of the invention including embodiments relating to the γ6 TM1a peptide can target Cav3.1 calcium current. In other embodiments, Cav1.2 calcium current is targeted.

EXAMPLE 3

Calcium Channel Proteins and Peptides

Peptide compositions can be designed as described herein and can be based on sequence information from mammalian versions of calcium channel proteins. See Table 4 which indicates sequence information with Accession Numbers from the NCBI Protein Database.

TABLE 4

| Accession Numbers from NCBI Protein Database. | | | |
|---|---|---|---|
| SEQUENCES | HUMAN | RAT | MOUSE |
| CACNG1 | AAH69493 | NM_019255 | NP_031608 |
| CACNG2 | AAH69612 | AF361339 | NP_031609 |
| CACNG3 | AAH37899 | AF361340 | NP_062303 |
| CACNG4 | AAF14538 | AF361341 | NP_062304 |
| CACNG5 | AAL50046 | AF361342 | NP_542375 |
| CACNG6 | AAL50047 | AF361343 | NP_573446 |
| CACNG7 | AAL50048 | AF361345 | AAL50044 |
| CACNG8 | AAL50049 | AF361346 | NP_573453 |
| TMEM37 | NP_899063 | NP_620795 | NP_062305 |

REFERENCES

App. Serial PCT US06/038179 by Best et al., filed Sep. 29, 2006 (published as International Publication No. WO/2007/041360 on Apr. 12, 2007) for Peptides and Calcium Regulation in Mammalian Cells;
U.S. application Ser. No. 11/537,323 by Best et al., filed Sep. 29, 2006 (published as Publication No. US 20070213267 on Sep. 13, 2007) for Peptides and Calcium Regulation in Mammalian Cells;
App. Ser. U.S. 61/047,929 by Best et al., filed Apr. 25, 2008; App. Ser. U.S. 60/722,707 by Best et al., filed Sep. 30, 2005; each of these applications is incorporated by reference in entirety.
Lear J D, Stouffer A L, et al., 2004, Association of a model transmembrane peptide containing gly in a heptad sequence motif, Biophys J 87:3421-3429.
Raybaud A, Dodier Y, Bissonnette P, Simoes M, Bichet D G, Sauvé R, Parent L. The role of the GX9GX3G motif in the gating of high voltage-activated Ca2+ channels. J Biol. Chem. 2006 Dec. 22; 281 (51):39424-36. Epub 2006 Oct. 11.
Raybaud A, Baspinar E E, Dionne F, Dodier Y, Sauvé R, Parent L. The role of distal S6 hydrophobic residues in the voltage-dependent gating of CaV2.3 channels. J Biol. Chem. 2007 Sep. 21; 282(38):27944-52. Epub 2007 Jul. 27.
Roth L, Nasarre C et al., Transmembrane domain interactions control biological functions of neuropilin-1, 2008 Mol Biol Cell 19(2):646-654.
Gorman P M, Kim S, et al., 2008, Dimerization of the transmembrane domain of amyloid precursor proteins and familial Alzheimer's disease mutants, BMC Neurosci. 9:17.
Munter L M et al., EMBO J. 2007 Mar. 21; 26(6):1702-12; GxxxG motifs within the amyloid precursor protein transmembrane sequence are critical for the etiology of Abeta42.
McClain M S, et al., J Biol. Chem. 2003 Apr. 4; 278 (14): 12101-8 12562777 Essential role of a GXXXG motif for membrane channel formation by *Helicobacter pylori* vacuolating toxin.
Sitte H H, et al, European Journal of Pharmacology Volume 479, Issues 1-3, 31 Oct. 2003, Pages 229-236.
El Amri C, Nicolas P, 2008 March, Cell Mol Life Sci 65(6): 895-909, Plasticins: membrane-damaging peptides with 'chameleon-like' properties.
Kairys V, Michael K. Gilson, Burkhard Luy (2004) Structural model for an AxxxG-mediated dimer of surfactant-associated protein C, European Journal of Biochemistry Volume 271 Issue 11 Page 2086-2092, Jun. 2004.
U.S. Pat. No. 5,122,596 Phillips, et al. Jun. 16, 1992, Polypeptides useful as blockers of calcium channels; U.S. Pat. No. 5,599,559 by Phillips et al. Feb. 4, 1997, Calcium channel blocking polypeptide from agelenopsis aperta and therapeutic methods employing it.
U.S. Pat. Nos. 6,063,819; 5,968,838; 5,877,026; 5,807,821; 5,776,896; 5,756,663; 5,677,288; 5,585,396; 5,512,592; 5,281,693; U.S. Pat. No. 4,925,664 Jackson, et al. May 15, 1990. U.S. Pat. No. 6,365,337 by Letts, et al., Apr. 2, 2002, Genes encoding neuronal voltage-gated calcium channel gamma subunits.
Best P M, Lin Z, Chen R-S, Garcia T, 2006, Identification of critical residues in TM1 of the gamma6 subunit critical for its inhibitory effect on Cav3.1 calcium current, Biophys J. Volume 90, January 2006, ABSTRACT for Presentation Number 1906-Pos.
Schneider, D. (2004). "Rendezvous in a membrane: close packing, hydrogen bonding, and the formation of transmembrane helix oligomers." FEBS Lett 577(1-2): 5-8.
G Kleiger, R Grothe, P Mallick, and D Eisenberg. GXXXG and AXXXA: common alpha-helical interaction motifs in proteins, particularly in extremophiles. Biochemistry, 41(19):5990-7, 2002.
Friel, D D and Bean B P, J. Gen Physiol., Volume 91 Jan. 1988 1-27, Two ATP-activated Conductances in Bullfrog Atrial Cells (citing Yellen G. Nature. 1982 Mar. 25; 296(5855):

357-9, Single Ca2+-activated nonselective cation channels in neuroblastoma (discusses 'sewer-pipe' technique)).

Ren-Shiang Chen and Philip M. Best, Mol. Pharmacol. 2009 Feb. 4, A Small Peptide Inhibitor of the Low Voltage-Activated Calcium Channel Cav3.1. Published on Feb. 4, 2009 as doi:10.1124/mol.108.052654, MOL #52654, Running title: A Peptide Inhibitor of the Cav3.1 Channel.

C-S Chiang, C-H Huang, H. Chieng, Y-T Chang, D. Chang, J-J Chen, Y-C Chen, Y-H Chen, H-S Shin, K. P. Campbell and C-C Chen. 2009 Circulation Research 104:522-530, The Cav3.2 T-Type Ca Channel is Required for Pressure Overload-induced Cardiac Hypertrophy.

Kato A S, Siuda E R, Nisenbaum E S, Bredt D S, Neuron 2008 Sep. 25; 59(6):986-96. AMPA receptor subunit-specific regulation by a distinct family of type II TARPs.

Soto D, Coombs I D, Renzi M, Zonouzi M, Farrant M, Cull-Candy S G. Nat. Neurosci. 2009 March; 12(3):277-85. Selective regulation of long-form calcium-permeable AMPA receptors by an atypical TARP, gamma-5.

Cabral A, De Ross J, Castilho V M, Brandao M L, Nobre M J. Glutamate receptor antagonism in inferior colliculus attenuates elevated startle response of high anxiety diazepam-withdrawn rats. Neuroscience. 2009 Apr. 3.

Lin Z, Witschas K, Garcia T, Chen R S, Hansen J P, Sellers Z M, Kuzmenkina E, Herzig S and Best P M (2008) A critical GxxxA motif in the {gamma}6 calcium channel subunit mediates its inhibitory effect on Cav3.1 calcium current. J Physiol November 15, 586(Pt 22):5349-5366.

Any sequence listing information is part of the specification.

STATEMENTS REGARDING INCORPORATION BY REFERENCE AND VARIATIONS

All references mentioned throughout this application, for example patent documents including issued or granted patents or equivalents; patent application publications; unpublished patent applications; and non-patent literature documents or other source material; are hereby incorporated by reference herein in their entireties, as though individually incorporated by reference. In the event of any inconsistency between cited references and the disclosure of the present application, the disclosure herein takes precedence. Some references provided herein are incorporated by reference to provide information, e.g., details concerning sources of starting materials, additional starting materials, additional reagents, additional methods of synthesis, additional methods of analysis, additional biological materials, additional cells, and additional uses of the invention.

All patents and publications mentioned herein are indicative of the levels of skill of those skilled in the art to which the invention pertains. References cited herein can indicate the state of the art as of their publication or filing date, and it is intended that this information can be employed herein, if needed, to exclude specific embodiments that are in the prior art. For example, when composition of matter are claimed herein, it should be understood that compounds known and available in the art prior to Applicant's invention, including compounds for which an enabling disclosure is provided in the references cited herein, are not intended to be included in the composition of matter claims herein.

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Thus as used herein, comprising is synonymous with including, containing, having, or characterized by, and is inclusive or open-ended and does not exclude additional, unrecited elements or method steps. As used herein, "consisting of" excludes any element, step, or ingredient, etc. not specified in the claim description. As used herein, "consisting essentially of" does not exclude materials or steps that do not materially affect the basic and novel characteristics of the claim (e.g., relating to an active ingredient). In each instance herein any of the terms "comprising", "consisting essentially of" and "consisting of" may be replaced with at least either of the other two terms, thereby disclosing separate embodiments and/or scopes which are not necessarily coextensive. An embodiment of the invention illustratively described herein suitably may be practiced in the absence of any element or elements or limitation or limitations not specifically disclosed herein.

Whenever a range is disclosed herein, e.g., a temperature range, time range, composition or concentration range, or other value range, etc., all intermediate ranges and subranges as well as all individual values included in the ranges given are intended to be included in the disclosure. This invention is not to be limited by the embodiments disclosed, including any shown in the drawings or exemplified in the specification, which are given by way of example or illustration and not of limitation. It will be understood that any subranges or individual values in a range or subrange that are included in the description herein can be excluded from the claims herein.

The invention has been described with reference to various specific and/or preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be employed in the practice of the invention as broadly disclosed herein without resort to undue experimentation; this can extend, for example, to starting materials, biological materials, reagents, synthetic methods, purification methods, analytical methods, assay methods, and biological methods other than those specifically exemplified. All art-known functional equivalents of the foregoing (e.g., compositions, methods, devices, device elements, materials, procedures and techniques, etc.) described herein are intended to be encompassed by this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, preferred embodiments, and optional features, modification and variation of the concepts herein disclosed may be resorted to by those skilled in the art, and that such modifications and variations are considered to be within the scope of this invention as defined by the appended claims.

We claim:

1. An isolated peptide consisting of a sequence of 8 to 14 amino acids, wherein the sequence contains a $GX_3X_4X_4G$-like structural motif, and wherein the sequence comprises $X_1$-$X_2$-$X_3$-$X_4$-$X_5$-$X_6$-$X_7$-$X_8$ (SEQ ID NO:11); wherein $X_1$ is L, I, V, or F; $X_2$ is G, A, S, or T; $X_3$ is L, I, V, A, or F; $X_4$ is L, I, V, A, F, or T; $X_4$ is L, I, V, A, or F; $X_6$ is G, A, or S; and each $X_7$ and $X_8$ independently is L, I, V, A, or F; wherein said isolated peptide is capable of inhibiting voltage dependent calcium current in a cell.

2. The peptide of claim 1 wherein X1 is L, V, or F; X2 is G; at least two of X3, X4, and X5 are L, V, or F; and X6 is A.

3. The peptide of claim 1 wherein if X2 is other than G, X6 is G or A.

4. The peptide of claim 1 wherein X2 is G; X6 is A; and four of X1, X3, X4, X5, X7, and X8 are L, V, or F.

5. The peptide of claim 1 wherein the sequence comprises SEQ ID NO: 1.

6. The peptide of claim 1 wherein the sequence comprises SEQ ID NO:2.

7. The peptide of claim 1 comprises SEQ ID NO: 3.

8. The peptide of claim 1 comprises SEQ ID NO:4.

9. The peptide of claim 1 comprises SEQ ID NO:5.

10. The peptide of claim 1 comprises SEQ ID NO:6.

11. The peptide of claim 1 comprises SEQ ID NO:7.

12. A method of regulating a calcium channel comprising contacting said calcium channel with the peptide of claim 1.

13. The method of claim 12 wherein said calcium channel is a voltage dependent calcium channel.

14. The method of claim 12 wherein said calcium channel is a low voltage activated calcium channel.

15. The method of claim 12 wherein said calcium channel is a high voltage activated calcium channel.

16. The method of claim 14 wherein said calcium channel is a Cav3.1 channel.

17. The method of claim 12 wherein said regulating inhibits calcium current.

18. The method of claim 12 wherein said regulating is selective for a low voltage activated channel.

19. The method of claim 12 wherein said calcium channel is in a mammalian cell.

20. The method of claim 12 wherein said mammalian cell is a cell line, a cardiomyocyte, or a neuronal cell.

21. The method of claim 12 wherein said regulating is at least partially reversible.

22. A pharmaceutical composition comprising as an active ingredient an effective amount of the peptide according to claim 1.

23. The pharmaceutical composition of claim 22 further comprising a pharmaceutically acceptable carrier.

24. The peptide of claim 1 wherein each of X3, X4, and X5 independently is an aliphatic amino acid.

25. The peptide of claim 1 wherein the peptide consists of 9, 10, 11, 12, 13, or 14 amino acids.

26. The peptide of claim 1 wherein the peptide consists of eight amino acids.

27. The peptide of claim 26 wherein the sequence consists of SEQ ID NO:1, SEQ ID NO:2, SEQ ID NO:3, SEQ ID NO:4, SEQ ID NO:5, SEQ ID NO:6, or SEQ ID NO:7.

28. The peptide of claim 26 wherein the sequence consists of SEQ ID NO:1.

* * * * *

UNITED STATES PATENT AND TRADEMARK OFFICE
CERTIFICATE OF CORRECTION

PATENT NO. : 8,299,211 B2  
APPLICATION NO. : 12/429214  
DATED : October 30, 2012  
INVENTOR(S) : Philip M. Best et al.

It is certified that error appears in the above-identified patent and that said Letters Patent is hereby corrected as shown below:

In the Claims

In claim 1, column 35, line 14, please replace "wherein the sequence contains a GX3X4X4G-like structural motif" with -- wherein the sequence contains a GX3X4X5G-like structural motif --

In claim 1, column 35, line 19, please replace "X4 is L, I, V, A, F, or T; X4 is L, I, V, A, or F; X6" with -- X4 is L, I, V, A, F, or T; X5 is L, I, V, A, or F; X6 --

Signed and Sealed this
Twenty-fifth Day of February, 2014

Michelle K. Lee
*Deputy Director of the United States Patent and Trademark Office*